(12) United States Patent
Ahn et al.

(10) Patent No.: US 11,543,410 B2
(45) Date of Patent: Jan. 3, 2023

(54) METHODS AND APPLICATIONS OF ON-CHIP DRIED OR LYOPHILIZED CHEMILUMINESCENCE SUBSTRATE REAGENTS

(71) Applicant: University of Cincinnati, Cincinnati, OH (US)

(72) Inventors: Chong H. Ahn, Cincinnati, OH (US); Sthitodhi Ghosh, Cincinnati, OH (US); Atreyee Chakraborty, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 986 days.

(21) Appl. No.: 16/119,255

(22) Filed: Aug. 31, 2018

(65) Prior Publication Data
US 2019/0072547 A1   Mar. 7, 2019

Related U.S. Application Data

(60) Provisional application No. 62/553,436, filed on Sep. 1, 2017.

(51) Int. Cl.
*G01N 33/543* (2006.01)
*B01L 3/00* (2006.01)
(Continued)

(52) U.S. Cl.
CPC .... *G01N 33/54373* (2013.01); *B01L 3/50273* (2013.01); *B01L 3/502738* (2013.01);
(Continued)

(58) Field of Classification Search
CPC ....... G01N 33/54373; G01N 33/54366; G01N 21/76; G01N 2021/0328;
(Continued)

(56) References Cited

U.S. PATENT DOCUMENTS 5,275,785 A * 1/1994 May ................. G01N 33/54386
422/408
5,401,667 A * 3/1995 Koike .................. G01N 33/558
422/412

(Continued)

OTHER PUBLICATIONS

S. Ghosh et al, "A Functional Lab-On-A-Chip Compatible with Smartphones for Chemiluminescence Based ELISA"; ResearchGate Conference; Oct. 2016.
(Continued)

*Primary Examiner* — Christopher L Chin
(74) *Attorney, Agent, or Firm* — Dinsmore & Shohl

(57) ABSTRACT

A sensing device includes a sample loading chamber configured to receive a sample, a detection antibody drying or lyophilization chamber configured to receive a first portion of the sample, one or more substrate drying or lyophilization chambers configured to receive a second portion of the sample, and one or more reaction chambers connected to the detection antibody drying or lyophilization chamber and the one or more substrate drying or lyophilization chambers. The detection antibody drying or lyophilization chamber and one or more substrate drying or lyophilization chambers are placed in parallel between the sample loading chamber and the one or more reaction chambers.

24 Claims, 20 Drawing Sheets

(51) Int. Cl.
*G01N 21/76* (2006.01)
*G01N 21/03* (2006.01)

(52) U.S. Cl.
CPC .. *G01N 33/54366* (2013.01); *B01L 2200/027* (2013.01); *B01L 2200/0605* (2013.01); *B01L 2200/10* (2013.01); *B01L 2200/16* (2013.01); *B01L 2300/0663* (2013.01); *B01L 2300/08* (2013.01); *B01L 2300/088* (2013.01); *B01L 2300/0861* (2013.01); *B01L 2300/0883* (2013.01); *B01L 2400/0406* (2013.01); *B01L 2400/0487* (2013.01); *B01L 2400/0688* (2013.01); *G01N 21/76* (2013.01); *G01N 2021/0328* (2013.01); *G01N 2021/0346* (2013.01)

(58) Field of Classification Search
CPC ........ G01N 2021/0346; G01N 33/5302; B01L 3/50273; B01L 3/502738; B01L 2200/027; B01L 2200/0605; B01L 2200/10; B01L 2200/16; B01L 2300/0663; B01L 2300/08; B01L 2300/0861; B01L 2300/088; B01L 2300/0883; B01L 2400/0406; B01L 2400/0487; B01L 2400/0688

USPC ............ 435/287.9, 288.4, 288.5, 288.7, 968; 427/2.13; 422/505, 506, 417, 437, 412, 422/414, 502, 503, 504, 507; 436/514
See application file for complete search history.

(56) References Cited

U.S. PATENT DOCUMENTS 7,300,802 B2 * 11/2007 Paek .................... G01N 33/558
436/514
9,726,588 B2 * 8/2017 Hofmann .......... B01L 3/502746

OTHER PUBLICATIONS

S. Ghosh and Chong H. Ahn, "Lyphilizatoin of chemiluminescent substrate reagents for high-sensitive microchannel-based lateral flow assay (MLFA) in point-of care (POC) diagnostic system"; Analyst, 2019, 144, 2109-2119.

S. Ghosh et al, "A New Mobile Healthcare System Using Smartphone and Lab-On-A-Chip for On-Site Diagnostics of Malaria"; 21st International Cofnerence on Miniaturized Systems for Chemistry and Life Sciences (MicroTAS 2017) in Savannah, Georgia; Oct. 22-26, 2017.

* cited by examiner

400

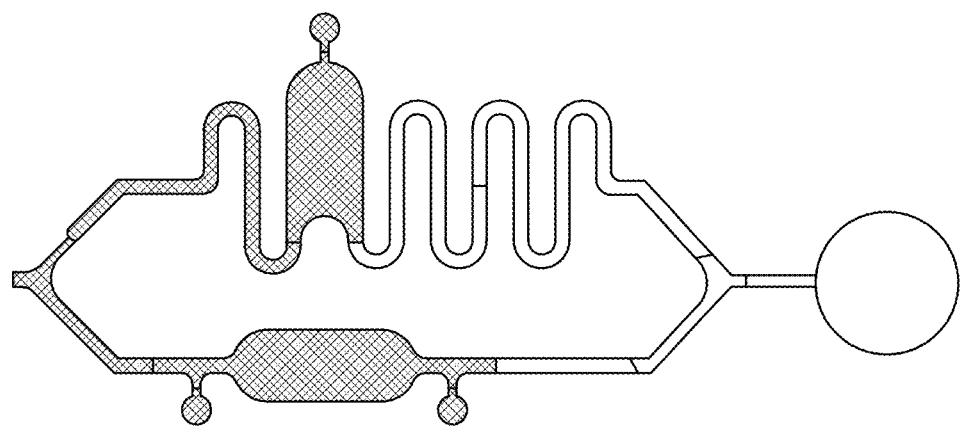
FIG. 7B (ii)
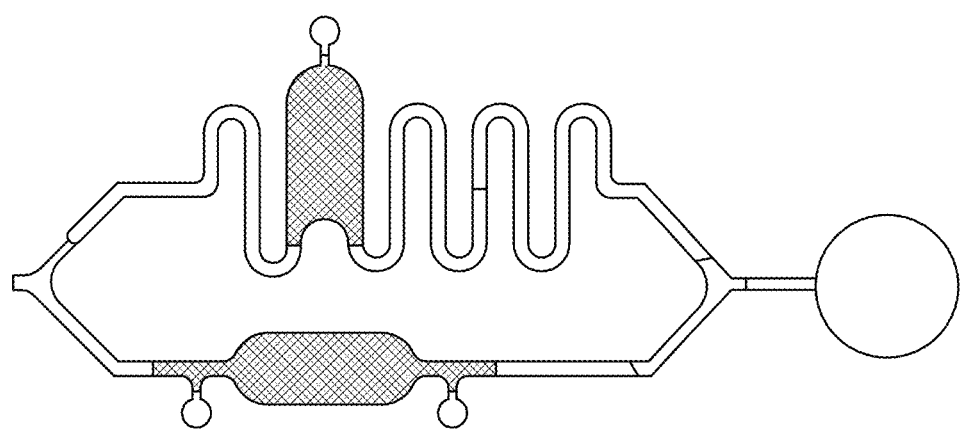
FIG. 7B (i)

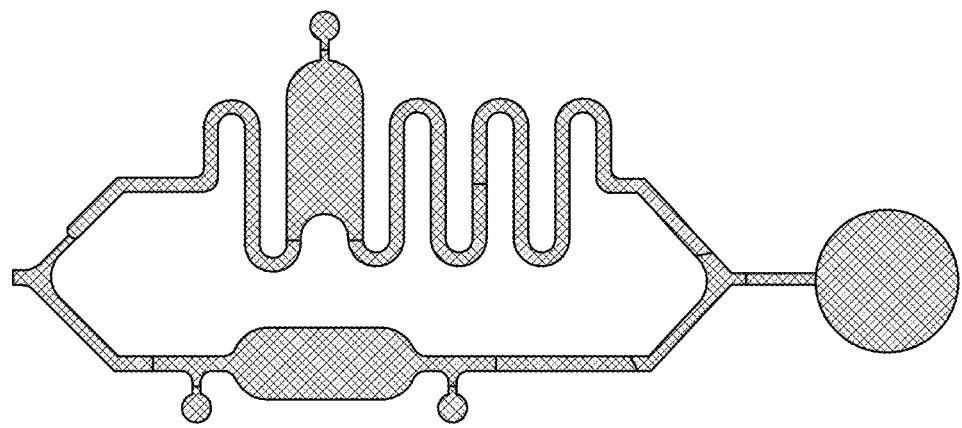
FIG. 7B (iv)
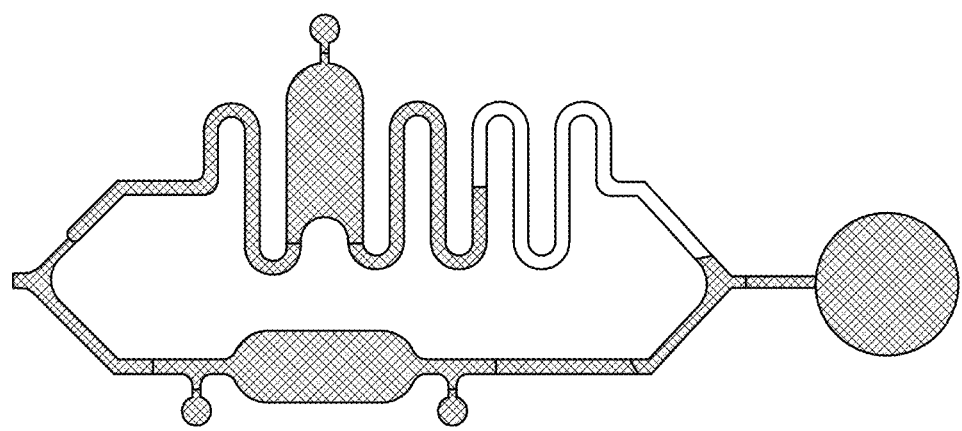
FIG. 7B (iii)

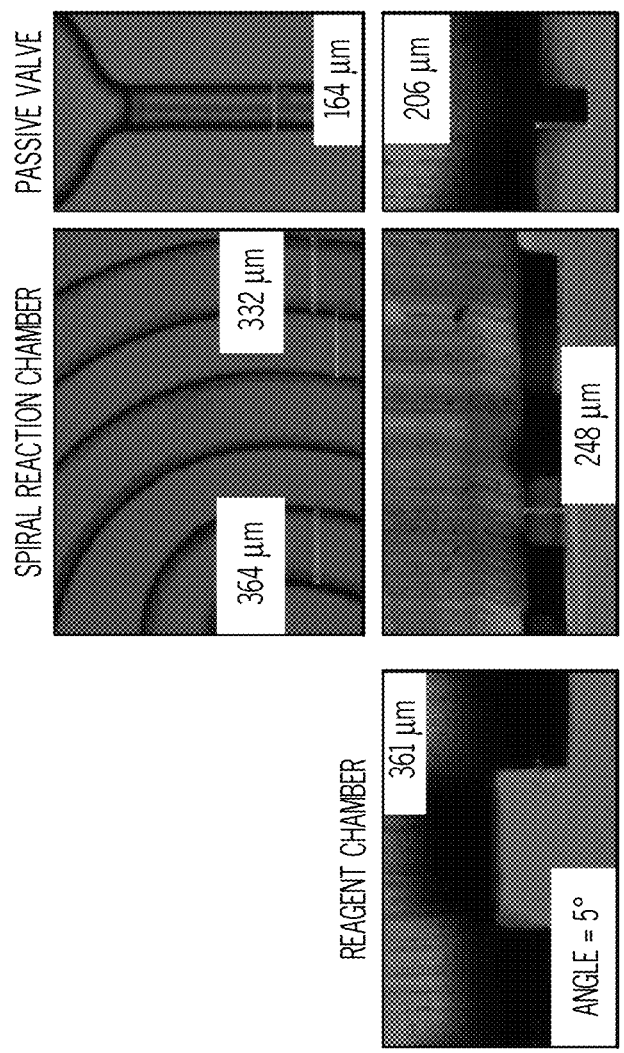

METHODS AND APPLICATIONS OF ON-CHIP DRIED OR LYOPHILIZED CHEMILUMINESCENCE SUBSTRATE REAGENTS

CROSS REFERENCE TO RELATED APPLICATIONS

This application claims priority to U.S. Provisional Application Ser. No. 62/553,436 filed Sep. 1, 2017, which application is hereby incorporated by reference in its entirety.

TECHNICAL FIELD

This disclosure relates to point-of-care test systems. More specifically, this disclosure relates to lab-on-a-chip devices having chambers for dried or lyophilized chemiluminescence substrate reagents and a chamber for dried or lyophilized detection antibody.

BACKGROUND

In recent years there has been a large demand in the development of simplified point-of-care testing (POCT) systems to rapidly detect the presence of a target biomarker in biological fluids for the diagnosis of diseases in resource limited settings. Developing reliable diagnostic tests that can be used at the point-of-care can result in earlier disease diagnosis, improved patient treatment, and more efficient outbreak prevention. An ideal point-of-care diagnostic system should consist of disposable cheap cartridges, a small volume of test sample, minimum human intervention and easily interpretable results. Lab-on-a-chip devices have several advantages over conventional immunodiagnostics methods, including fast and efficient separation of various analytes (from small ions to large biomolecules), providing a feasible method for conducting numerous experiments in parallel while consuming little reagent and achieving even better results. Other major advantages for microfluidic assays are miniaturization, small sample volume, portability, rapid detection time and higher sensitivity.

The limit of detection (LOD) of the POCT devices can be largely improved if enzyme-based signal amplification, commonly used for conventional Enzyme-linked Immunosorbent Assay (ELISA), is implemented in POCT devices. However, most of the research studies reported for implementing immunoassays in microfluidic format still involve multiple liquid handling steps including critical pipetting performed by trained personals which is a hindrance for the development of autonomous POCT systems. The user intervention can be minimized in sample-to-answer systems, in which the user needs only to put the sample in the system to get analytical answers without further intervention.

Standard commercially available assays mostly use optical detection methods like luminescence, fluorescence or absorbance. Therefore, to develop lab-on-a-chip (LOC) based POCT platforms with performance comparable to commercially available gold standard assay procedures optical detection methods are preferable. Several high sensitive completely integrated "sample-to-answer" LOC based POCT platforms have been developed which employs either absorbance (colorimetric) or fluorescence-based detection methods. However, most colorimetric and fluorescence detection systems lack either the desired sensitivity or are complicated to develop as they require some excitation mechanisms.

Another high sensitive detection method used for conventional ELISA is the chemiluminescence. Chemiluminescent signal is generated as light by the release of energy (photon) due to a chemical reaction. Unlike absorbance, colorimetric or fluorescent measurements, ELISA reagents typically contribute little or no native background chemiluminescent signal. Detection of chemiluminescent optical signal is relatively simple as it requires only a photomultiplier or photodiode and the associated electronics. The lack of inherent background and the ability to easily measure very low and very high light intensities with simple instrumentation provide a large potential dynamic range of measurement in case of chemiluminescence based assays.

Monitoring potential health hazards in workers exposed to airborne respirable nano or micro particles at worksites is an important issue and can help in early diagnosis and save lives. Many workers in work environments that involve mining, hydraulic fracturing or fracking, drilling and construction are routinely exposed to airborne respirable nano or micro particles. Inhalation of respirable nano or micro particles can cause lung cancer, pneumoconiosis and chronic obstructive pulmonary disease (COPD) and is considered as one of the most significant occupational health problems. Early detection and biomonitoring of pulmonary responses to respirable nano or micro particle exposure, such as lung inflammation and oxidative stress as well as early identification of on-set of any pulmonary diseases in workers, are of great importance. The currently available diagnostic procedures to identify lung inflammation and pulmonary diseases in patients are based on chest radiography and conventional laboratory-based immunoassays for analyzing the pulmonary disease biomarkers which are highly sensitive and useful. However, the conventional diagnostic methods may not allow frequent monitoring of samples from exposed workers due to the time-consuming nature of testing, multiple handling procedures and need for trained personnel. For successful on-site biomonitoring, new methods are required that are portable and can provide reliable data quickly and accurately. Thus, there has been a large demand for the development of a low cost, field-portable functional LOC based POCT diagnostic method that can provide data quickly and accurately at the work sites.

Therefore, a need exist for developing POCT platform comprised of disposable thermoplastic polymer based functional LOC and chemiluminescent based portable analyzer for high sensitive biomarker detection.

SUMMARY

The present disclosure dries the assay reagents on the assay device prior to sample addition and to control the flow of the biological fluid through the drying chambers resulting in reconstitution of the reagents. For low resource setting applications, dry-form reagent storage is particularly important for its ability to preserve reagent function in environments with high local temperatures and a lack of refrigeration. Lyophilization may be considered as one of methods of drying reagents.

The present disclosure demonstrates a portable, easy-to-use, disposable functional lab-on-a-chip (LOC) containing on-chip lyophilized reagents. The developed LOC was characterized for early detection of biomarkers Tumor Necrosis Factor-α (TNF-α) related to pulmonary effects caused by exposure of toxic airborne respirable nano or micro particles. TNF-α, a 17 kDa pro-inflammatory cytokine is released during the early on-set of lungs tissue inflammation and other pulmonary diseases and hence was considered as one of the potential biomarkers in the present disclosure to be used for early detection of pulmonary diseases caused by airborne respirable nano or micro particles. The sandwich chemiluminescent enzyme-linked immunosorbent assay (ELISA) performance of the developed LOC was also optimized to detect very low concentration of TNF-α. Such a device has the capability to transform exposure monitoring and surveillance based on external (e.g., air, surface) measurements to on-site bio-monitoring or health monitoring at work places. Availability of such a POCT system could provide early detection of disease markers so that health risks could be potentially eliminated or reduced through early intervention and treatment.

In one embodiment, a sensing device includes a sample loading chamber configured to receive a sample, a detection antibody drying or lyophilization chamber configured to receive a first portion of the sample, one or more substrate drying or lyophilization chambers configured to receive a second portion of the sample, and one or more reaction chambers connected to the detection antibody drying or lyophilization chamber and the one or more substrate drying or lyophilization chambers. The detection antibody drying or lyophilization chamber and one or more substrate drying or lyophilization chambers are placed in parallel between the sample loading chamber and the one or more reaction chambers.

In another embodiment, a method of testing a sample on the sensing device is described. The two methods such as air pressure-driven pumping method and capillary force-driven pumping method, which are adopted to drive flow the sample through the microchannels or chambers, includes providing the sample in the sample loading chamber (a) for the air-driven method, turning on an air pump to provide air to the sample in the sample loading chamber such that the first portion of the sample flows into the detection antibody drying or lyophilization chamber and the second portion of the sample flows into the one or more substrate drying or lyophilization chambers after the first portion of the sample flows into the detection antibody drying or lyophilization chamber, turning off the air pump for a predetermined time, and turning on the air pump, after the predetermined time, to provide air to the sample such that the first portion of the sample flows into the one or more reaction chambers, and the second portion of the sample flows into the one or more reaction chambers after the first portion of the sample flows into the one or more reaction chambers and (b) for the capillary force-driven method, if the sample is loaded in the sample loading chamber, then the sample flows through the series of microchannels by the capillary forces which are produced by the sample through the microchannels. The flow rates and sequences of the sample are depending on the dimension and structure of the microchannels, microchambers and embedded microstructures. The flow sequence is such that the first portion of the sample flows into the detection antibody drying or lyophilization chamber and the second portion of the sample flows into the one or more substrate drying or lyophilization chambers after the first portion of the sample flows into the detection antibody drying or lyophilization chamber, passing inclined structures or embedded structures in the microchannels or chambers as time delay for better reconstitution of the substrate and antibody, then the sample such that the first portion of the sample flows into the one or more reaction chambers, and the second portion of the sample flows into the one or more reaction chambers after the first portion of the sample flows into the one or more reaction chambers.

In yet another embodiment, a sensing system includes a sensing device and an analyzer. The sensing device includes a sample loading chamber configured to receive a sample, a detection antibody drying or lyophilization chamber comprising dried or lyophilized detection antibodies, the detection antibody drying or lyophilization chamber being configured to receive a first portion of the sample, one or more substrate drying or lyophilization chambers comprising dried or lyophilized substrates, the one or more substrate drying or lyophilization chambers being configured to receive a second portion of the sample, and one or more reaction chambers connected to the detection antibody drying or lyophilization chamber and the one or more substrate drying or lyophilization chambers. The detection antibody drying or lyophilization chamber and one or more substrate drying or lyophilization chambers are placed in parallel between the sample loading chamber and the one or more reaction chambers.

These and other objects, features, embodiments, and advantages will become apparent to those of ordinary skill in the art from a reading of the following detailed description and the appended claims.

BRIEF DESCRIPTION OF THE DRAWINGS

FIG. 7B depicts a flowing sequence of a sample in the chip, according to one or more embodiments shown and described herein;

FIG. 11A depicts the structural analysis picture of a reagent chamber of a replicated lab-on-a-chip device;

FIG. 11B depicts the structural analysis picture of a spiral reaction chamber of a replicated lab-on-a-chip device;

FIG. 11C depicts the structural analysis picture of a hydrophobic passive valve of a replicated lab-on-a-chip device;

DETAILED DESCRIPTION

Figure 1:
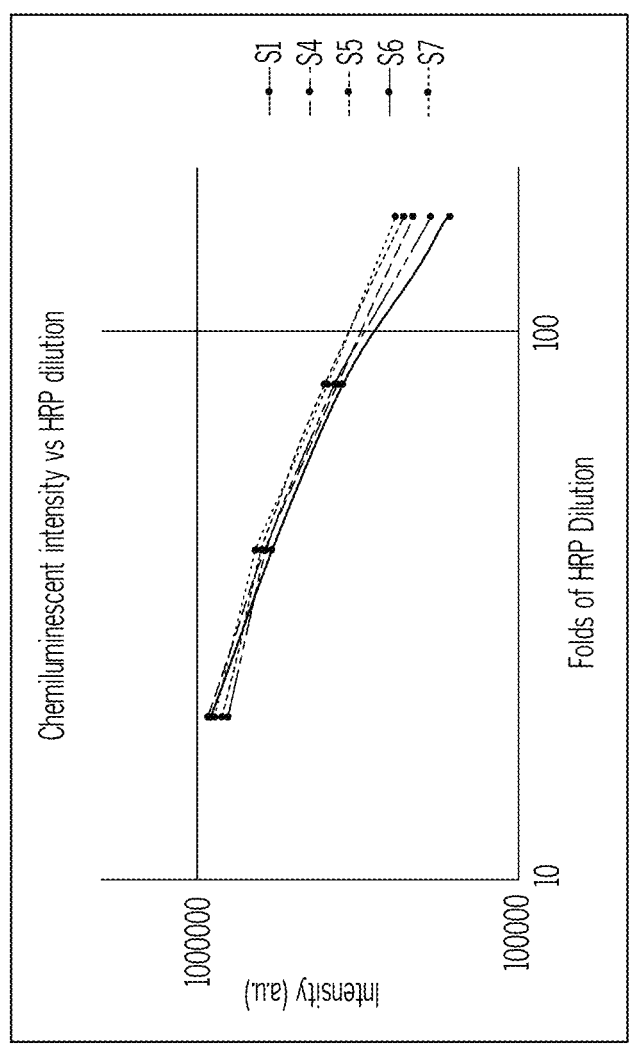
FIG. 1 depicts chemiluminescent intensity with respect to different concentrations of HRP for different conditions of substrate drying.

The details of one or more embodiments of the presently-disclosed subject matter are set forth in this document. Modifications to embodiments described in this document, and other embodiments, will be evident to those of ordinary skill in the art after a study of the information provided herein.

While the following terms are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, pH, size, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

An "effective amount," as used herein, refers to an amount of a substance (e.g., a therapeutic compound and/or composition) that elicits a desired biological response. In some embodiments, an effective amount of a substance is an amount that is sufficient, when administered to a subject suffering from or susceptible to a disease, disorder, and/or condition, to treat, diagnose, prevent, and/or delay and/or alleviate one or more symptoms of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of a formulation to treat a disease, disorder, and/or condition is the amount that alleviates, ameliorates, relieves, inhibits, prevents, delays onset of; reduces severity of and/or reduces incidence of one or more symptoms or features of the disease, disorder, and/or condition. Furthermore, an effective amount may be administered via a single dose or via multiple doses within a treatment regimen. In some embodiments, individual doses or compositions are considered to contain an effective amount when they contain an amount effective as a dose in the context of a treatment regimen. Those of ordinary skill in the art will appreciate that a dose or amount may be considered to be effective if it is or has been demonstrated to show statistically significant effectiveness when administered to a population of patients; a particular result need not be achieved in a particular individual patient in order for an amount to be considered to be effective as described herein.

Drying or Lyophilization of Chemiluminescent Substrate

In embodiments, chemiluminescent substrate may be dried or lyophilized on a lab-on-a-chip device. The chemiluminescence substrate is obtained in 2 parts (the enhancer and the peroxide) which are to be mixed in equal ratio to obtain the final form. Thermo Scientific™ SuperSignal™ chemiluminescent HRP substrates offer good performance in western blotting applications, with longer light emission and stronger signal intensity than other luminol-based detection systems and were used for the experiments. The enhancer and the peroxide are available in liquid form. Vacuum may be employed as a process for removing bulk and absorbed water or solvent from a product. Combined with heat and cool, vacuum may be an effective method for drying. High degrees of dryness may be attained at relatively low temperatures. This allows for fast and effective drying of temperature sensitive products. In embodiments, the samples are dried at 37° C. in a vacuum oven for 2 hours. In some embodiments, the reagents are freeze dried in Labconco™ freeze-dryer system. The liquids are first pre-frozen in liquid nitrogen and then are freeze dried in the Labconco™ freezer system at −54° C. and 0.010 mbar pressure. In order to fulfill the objective of substrate lyophilization, 7 different conditions are tested as shown in the table 1 below:

TABLE 1

|  | Substrate A (enhancer) | Substrate B (Peroxide) | Mix Volume | Mix Ratio | Dried | Reconstituted Volume (PBS) | Centrifuge (9000 rpm-15 min) |
|---|---|---|---|---|---|---|---|
| Sub1 | 100 μL | 100 μL | 200 μL | 1:1 | No | | |
| Sub2 | 100 μL | 100 μL | 200 μL | 1:1 | Yes | 200 μL | Yes |
| Sub3 | 100 μL | 100 μL | 200 μL | 1:1 | Yes | 200 μL | No |
| Sub4 | 100 μL (dried) | 100 μL (dried) | | | Yes | 100 μL + 100 μL | Yes |
| Sub5 | 100 μL (dried) | 100 μL (dried) | | | Yes | 100 μL + 100 μL | No |
| Sub6 | 100 μL (dried) | 100 μL (dried) | | | Yes | 200 μL | Yes |
| Sub7 | 100 μL (dried) | 100 μL (dried) | | | Yes | 200 μL | No |

Sub1 in Table 1 refers to the normal condition where the enhancer and the peroxide are mixed in equal ratio in liquid form and is used as the reference. In case of Sub2 and Sub3, the enhancer and peroxide are first mixed in liquid form and then dried. The reconstituted volume is centrifuged for Sub2 and used as it is for Sub3. For all the other 4 conditions, the enhancer and the peroxide are individually dried and then reconstituted either individually (in case of Sub4 and Sub5) or sequentially (in case of Sub6 and Sub7). The presence or absence of centrifuge post reconstitution creates the further distinction. The HRP solution was diluted in PBS to obtain different concentrations of HRP. HRP-substrate assay is performed using 96-well Optimizer™ microplate and chemiluminescent signal output is measured by off-line reader (BioTek, Synergy H1). FIG. 1 shows the results as obtained. As evident from the results, Sub2 and Sub3 do not show in chemiluminescent output whereas Sub4-7 show prominent results validating the proposition that chemiluminescence assay may be performed with reagents that were previously dried.

Figure 2:
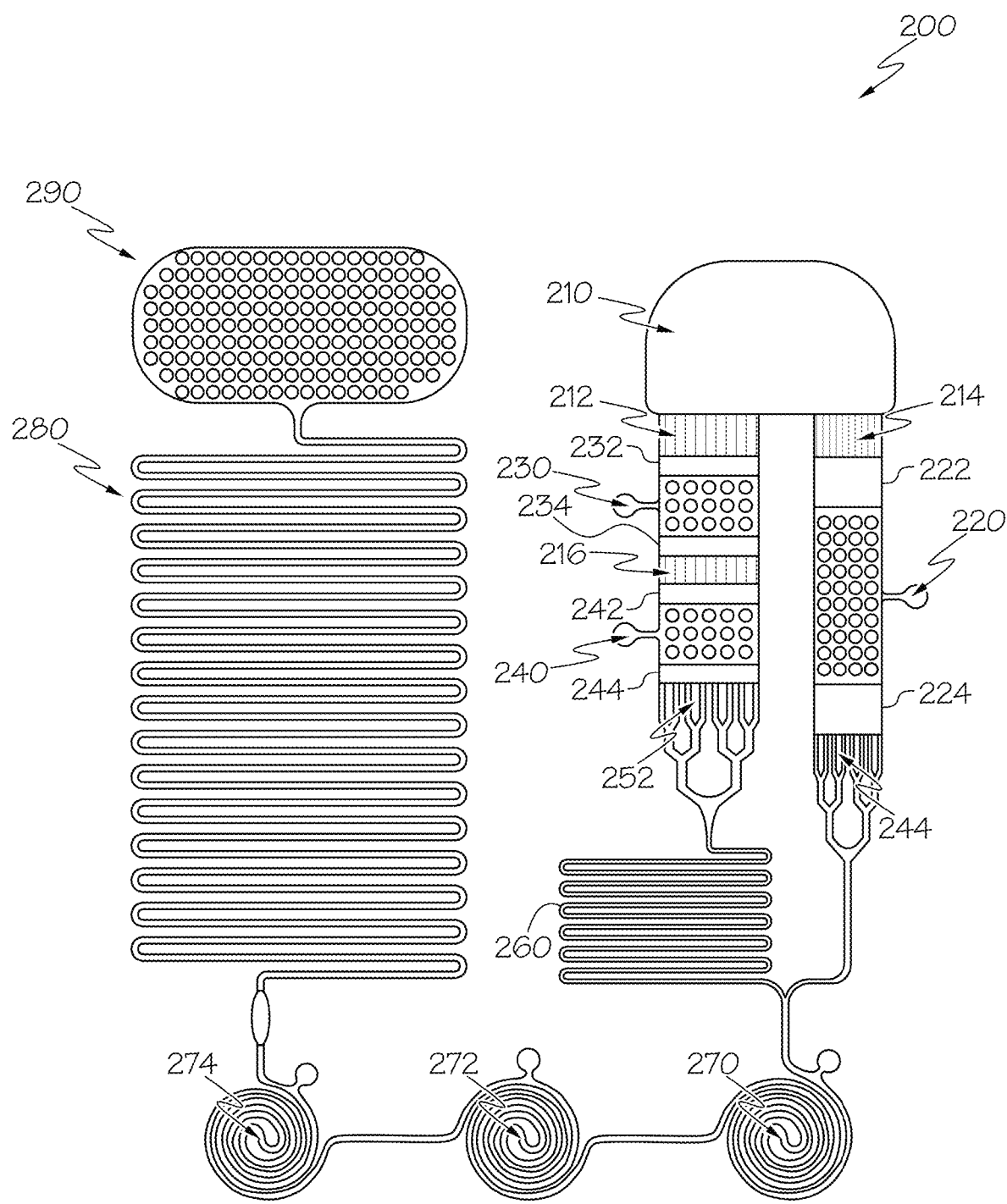
FIG. 2 depicts the schematic diagram of a conceptualized lateral flow based lab-on-a-chip according to one or more embodiments shown and described herein.

Dry Reagent Based Chemiluminescent Assay on Polymer Chip Using Capillary Force-Driven Flow FIG. 2 shows the schematic diagram of a conceptualized lateral flow based lab-on-a-chip device 200 according to one or more embodiments shown and described herein.

The lab-on-a-chip device 200 as shown in FIG. 2 includes a sample reservoir 210, a detection antibody drying or lyophilization chamber 220, a first substrate drying or lyophilization chamber 230, a second substrate drying or lyophilization chamber 240, a first delay channel 260, a plurality of reaction chambers 270, 272, 274, a second delay channel 280, and a capillary pump 290. A first set of capillary channels 212 are placed between the sample reservoir 210 and the first substrate drying or lyophilization chamber 230 as shown in FIG. 2. A second set of capillary channels 214 are placed between the sample reservoir 210 and the detection antibody drying or lyophilization chamber 220 as shown in FIG. 2. A third set of capillary channels 216 are placed between the first substrate drying or lyophilization chamber 230 and the second substrate drying or lyophilization chamber 240 as shown in FIG. 2. A first multiplexing capillary channel 252 is placed between the second substrate drying or lyophilization chamber 240 and the first delay channel 260 as shown in FIG. 2. A second multiplexing capillary channel 254 is placed between the detection antibody drying or lyophilization chamber 220 and the reaction chamber 270 as shown in FIG. 2.

The sample reservoir 210 is designed to have a volume of around 20 microliter (μL) and is in direct fluidic contact with the first set of capillary channels 212 and the second set of capillary channels 214. The first set and second set of capillary channels 212 and 214 are narrow microfluidic channels which prevent the diffusion of reconstituted mixture in the first substrate drying or lyophilization chamber 230 or the detection antibody drying or lyophilization chamber 240 back into the sample reservoir 210 and helps in fluid stopping and incubation.

As compared to colorimetric and fluorescent assay, the chemiluminescence assay involves the addition of substrate for the reaction. Thus, the lab-on-a-chip device 200 involves two parallel paths: one path incorporates the HRP labelled detection antibody drying or lyophilization chamber 220 and the other path has the substrate drying or lyophilization chambers 230, 240. In embodiments, the two components of the chemiluminescent substrate, namely the enhancer and the peroxide, need to be dried or lyophilized individually on the lab-on-a-chip device 200. Hence, the first substrate drying or lyophilization chamber 230 and the second substrate drying or lyophilization chamber 240 are envisaged on the lab-on-a-chip device 200. The enhancer may be dried or lyophilized in the first substrate drying or lyophilization chamber 230 and the peroxide may be dried or lyophilized in the second substrate drying or lyophilization chamber 240. The HRP labelled detection antibody may be dried or lyophilized in the detection antibody drying or lyophilization chamber 220.

The surface of each of the detection antibody drying or lyophilization chamber 220, the first substrate drying or lyophilization chamber 230, and the second substrate drying or lyophilization chamber 240 include circular posts 221, 231, and 241, respectively, to facilitate drying or lyophilization of reagents on the surface during drying of reagents. In absence of the posts 221, 231, and 241, the fluid to be dried tend to form larger menisci at the corners and produce a non-uniform layer of dried reagent. The presence of the textures causes the creation of numerous small menisci and results in uniform drying.

A first descending passage 232 is located between the first set of capillary channels 212 and the first substrate drying or lyophilization chamber 230. A first ascending passage 234 is located between the first substrate drying or lyophilization chamber 230 and the third set of capillary channels 216. A second descending passage 242 is located between the third set of capillary channels 216 and the second substrate drying or lyophilization chamber 240. A second ascending passage 244 is located between the second substrate drying or lyophilization chamber 240 and the first multiplexing capillary channel 252. A third descending passage 222 is located between the second set of capillary channels 214 and the detection antibody drying or lyophilization chamber 220. A third ascending passage 224 is located between the detection antibody drying or lyophilization chamber 220 and the second multiplexing capillary channel 254. The descending passages 222, 232, 242 prevent reverse flow of the sample (e.g., flow of the sample from the first substrate drying and lyophilization chamber 230 to the first set of capillary channels 212). The ascending passages 224, 234, and 244 delay the flow of the sample to the next step (e.g., flow of the sample from the first substrate drying or lyophilization chamber 230 to the third set of capillary channels 216).

The first multiplexing capillary channel 252 at the end of the second substrate drying and lyophilization chamber 240 and the second multiplexing capillary channel 254 at the end of the detection antibody drying or lyophilization chamber 220 facilitate the collection of liquid without the incorporation of air bubbles and with low dead volume. The first and second delay channels 260 and 280 in the substrate path delay the fluid flow and allow the antigen-detection antibody complex to bind with the immobilized capture antibody in the reaction chambers 270, 272, and 274.

The flow resistance of the first delay channel 260 is so calculated that the sample reconstituting the dried or lyophilized detection antibody in the detection antibody drying or lyophilization chamber 220 will reach the end of the reaction chambers 270, 272, 274 before the sample reconstituting the dried or lyophilized substrates in the substrate drying or lyophilization chambers 230 and 240 enters the reaction chambers 270, 272, 274. The spiral reaction chambers 270, 272, 274 have higher surface-to-volume ratio when compared to a well of conventional 96-well plate. The high surface-to-volume ratio results in higher amount of capture antibody immobilization. This results in high optical signal output with small sample volume. The meandering structure following the reaction chambers 270, 272, 274 retards the flow and allows for longer incubation in the reaction chambers 270, 272, 274.

The capillary pump 290 provides a higher flow rate for washing of unbounded reagent. The reaction between the reconstituted substrate and immobilized complex in the reaction chambers 270, 272, 274 will produce the desired chemiluminescent light.

The working of chemiluminescence based sandwich ELISA is validated on the polymer lab-on-a-chip using mouse tumor necrosis factor-α (TNF-α) as a demonstrate vehicle. Protocol optimization steps are carried out to determine the best possible capture antibody and detection antibody concentrations. The optimal capture and detection antibody concentrations are selected as 2.4 µg/mL and 0.6 µg/mL respectively due to the saturation of the signal after that point and lowest CV %. For the initial experiments human serum is spiked with antigen being used. The sample concentration is varied from 2,000 pg/ml to 100 pg/ml.

The spiral reaction chambers 270, 272, 274 shown in FIG. 2 have a volume of around 2.5 pt. The spiral reaction chamber has higher surface-to-volume ratio when compared to a well of conventional 96-well plate. The high surface-to-volume ratio results in higher amount of capture antibody immobilization. This results in high optical signal output with small sample volume. The spiral reaction chambers 270, 272, 274 are treated as followings. Capture antibodies are coated onto the spiral reaction chamber 270, 272, 274 by surface immobilization. The unbounded antibodies are washed by the washing buffer solution. Then, the blocking buffer solution is incubated to reduce non-specific protein adsorption on the surface. In the assay, artificial human serum spiked with antigen is used as a sample. The sample is delivered to the reaction chambers 270, 272, 274 followed by dried-and-reconstituted HRP conjugated detection antibody. The unbounded reagents are washed by adding the washing buffer solution and finally the dried-and-reconstituted chemiluminescent substrate are added. While FIG. 2 depicts three reaction chambers connected in series, more than or less than three reaction chambers may be used.

Figure 3:
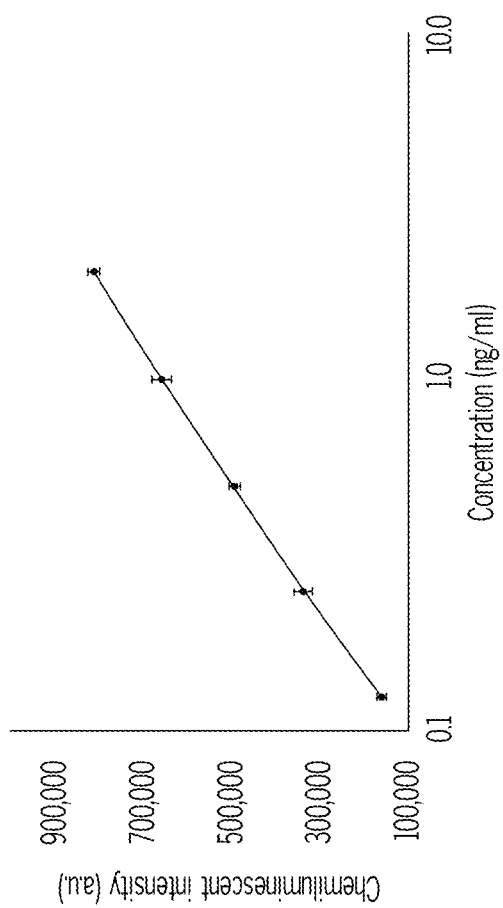
FIG. 3 depicts measured results of chemiluminescence assay for mouse TNF-alpha.

The obtained assay results are shown in FIG. 3. The result shows a proportional increase of the emitted chemiluminescent light with the increase of the concentration of TNF-alpha antigen validating the functioning of assay reagents on the cyclic olefin copolymer (COC) chips. These preliminary results show that the fabricated functional polymer lab-on-a-chips may be developed for the high sensitive detection of malarial biomarkers.

Figure 4:
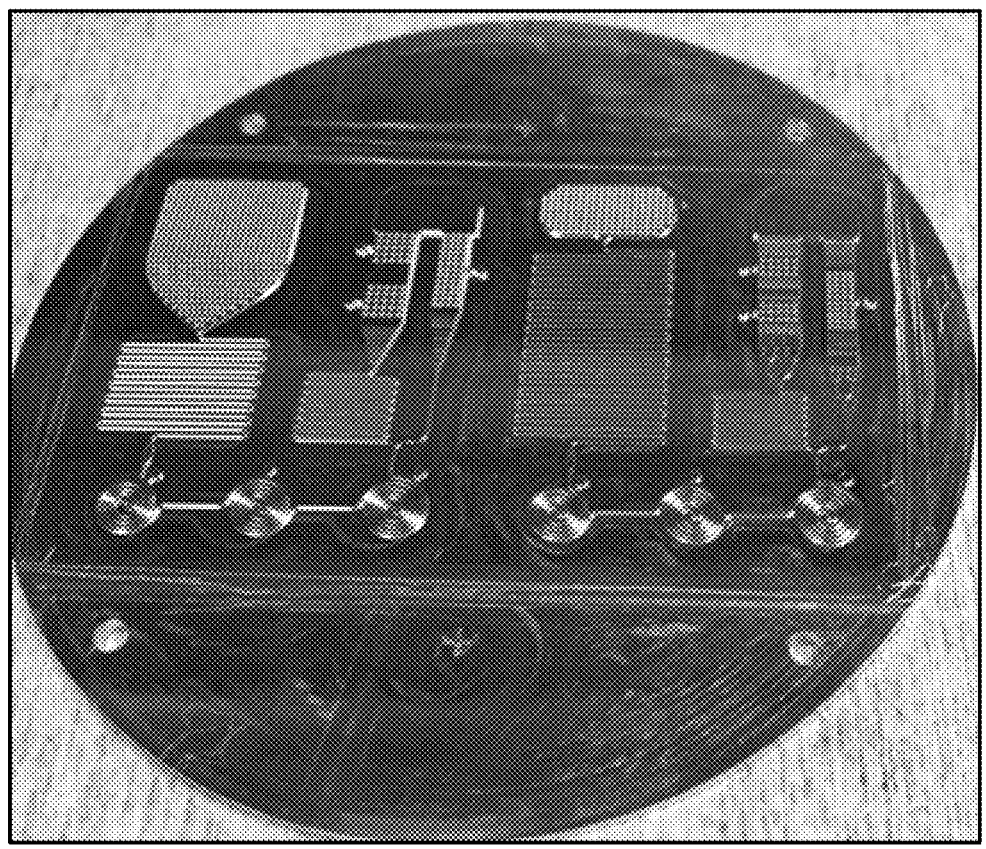
FIG. 4 depicts an aluminum mastermold, according to one or more embodiments shown and described herein.
Figure 5:
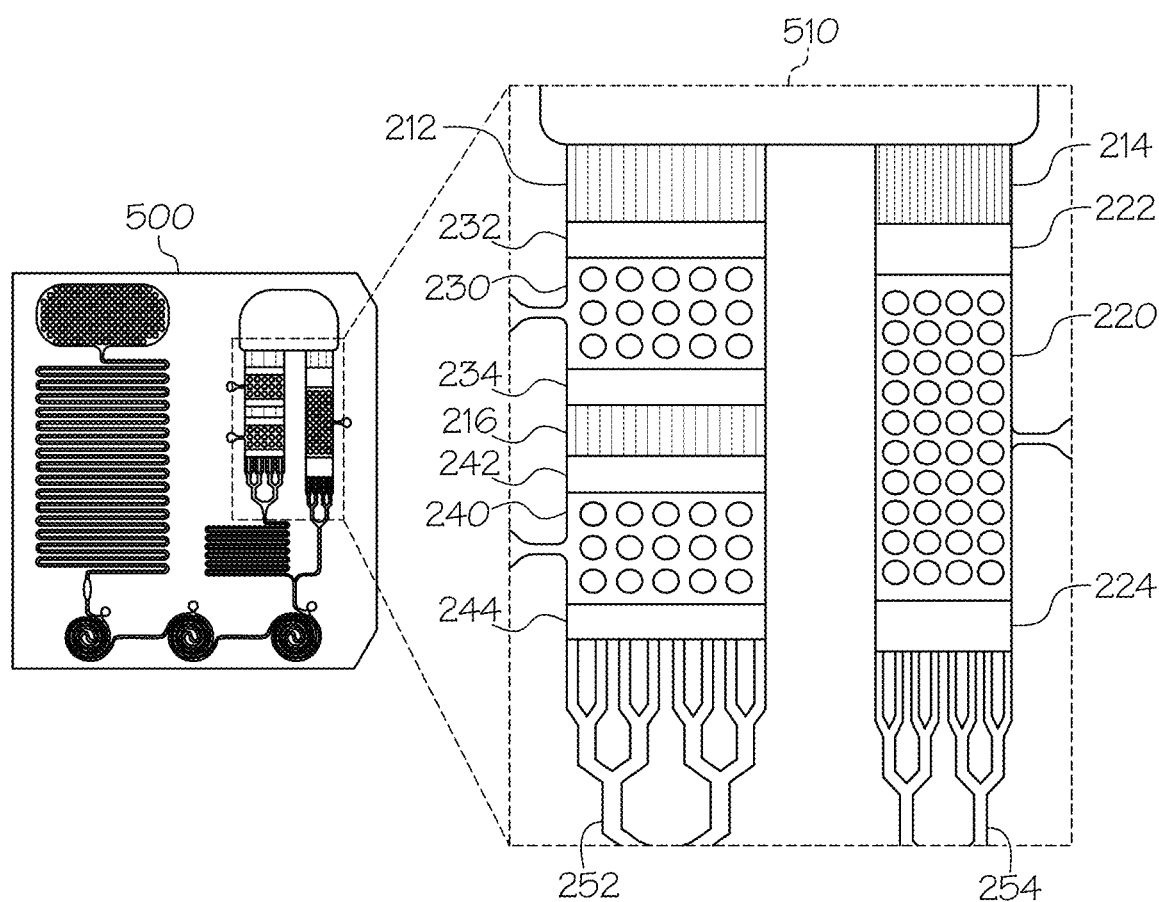
FIG. 5 depicts a fabricated COC chip with features magnified, according to one or more embodiments shown and described herein.

The fabrication process consisted of mold designing, aluminum micromachining and polymer chip replication using injection molding. The lab-on-a-chip device 200 is designed in the MasterCam™ software and the toolpaths are created which can be directly fed to the CNC milling machine for micromold fabrication. Aluminum alloy is used as the master mold material shown in FIG. 4 since it is flexibly machinable and can run for several thousand replication cycles under optimized replication cycles. Thermoplastic polymer cyclic olefin copolymer (COC) is used as the substrate material for the polymer lab-on-a-chips. COC is used because of its high affinity towards surface immobilization of antibodies, high resistance towards polar solvents, very high flow rates during injection molding and excellent optical transparency. The fabricated COC chip with features magnified is shown in FIG. 5.

Figure 6A:
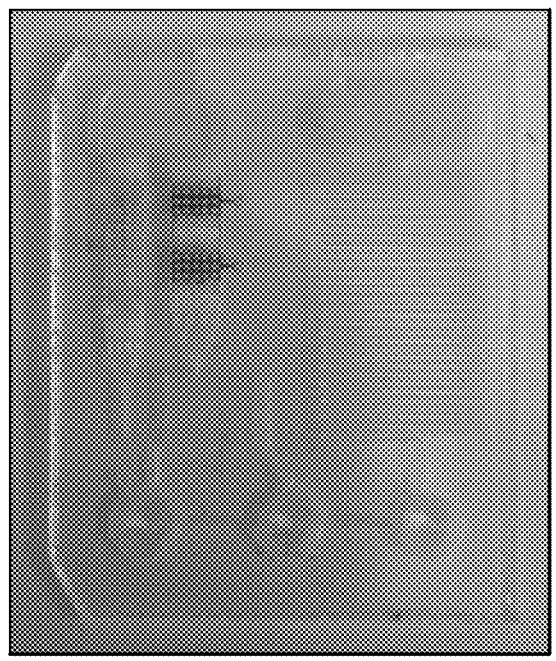
FIG. 6A depicts a lab-on-a-chip before lyophilization, according to one or more embodiments shown and described herein.
Figure 6B:
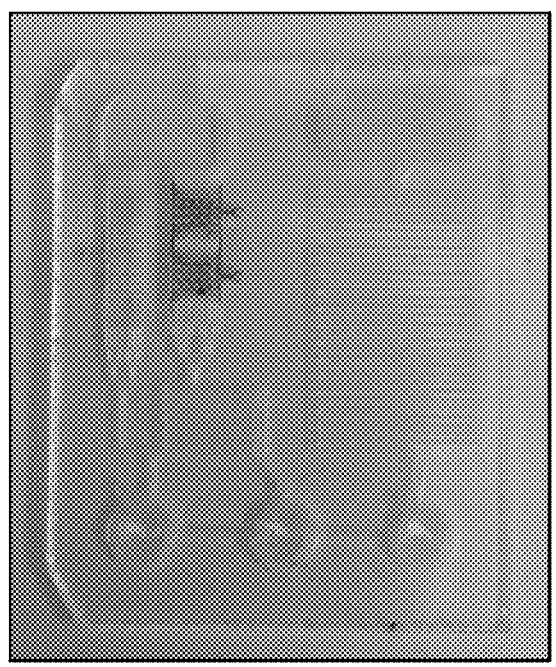
FIG. 6B depicts a lab-on-a-chip after lyophilization, according to one or more embodiments shown and described herein.
Figure 6C:
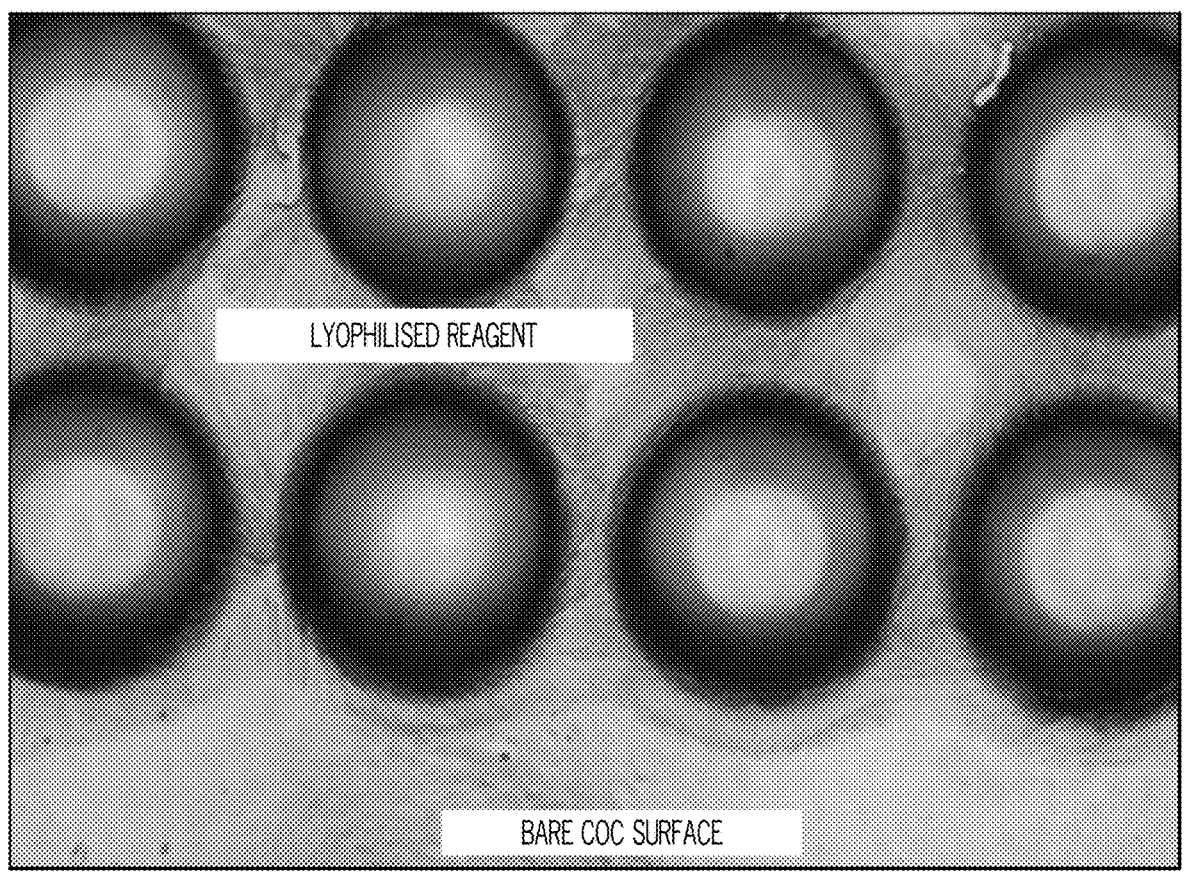
FIG. 6C depicts a lab-on-a-chip having lyophilized reagents, according to one or more embodiments shown and described herein.

FIGS. 6A through 6C show the lab-on-a-chip before and after lyophilization. A dye is mixed with the reagents for better visibility. FIG. 6A shows a polymer lab-on-a-chip with liquid reagents added to the drying chambers. FIG. 6B shows the same chip after reagent lyophilization. FIG. 6C shows magnified image of the drying chamber (e.g., the first and second substrate drying or lyophilization chambers 230 and 240, and the antibody detection drying or lyophilization chamber 220) after lyophilization showing the uniform drying of the reagents on the polymer surface. In embodiments, the designed geometry of the drying or lyophilization chambers 220, 230, and 240 confines the reagents in the respective chambers prior to drying thus eliminating the problem of mixing and contamination. Liquid reagents are added to the respective chambers and are freeze-dried at −54 degrees Celsius and 0.010 mbar pressure.

Figure 7A:
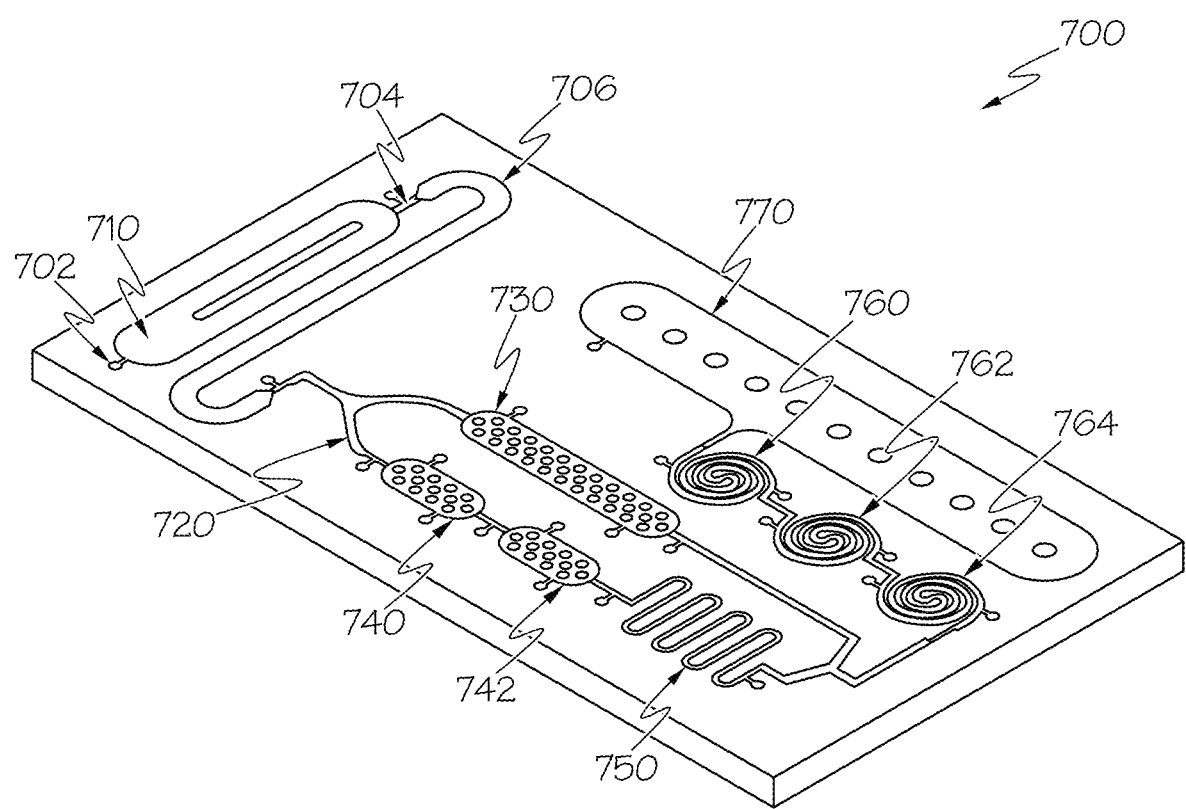
FIG. 7A depicts a schematic diagram of a lab-on-a-chip device, according to one or more embodiments shown and described herein.

Dry Reagent Based Lab-On-a-Chip Concept and Principle of Air Pressure-Driven Assay FIG. 7A depicts a schematic diagram of a lab-on-a-chip device 700, according to one or more embodiments shown and described herein. The overall dimensions of the lab-on-a-chip device 700 are 60 mm×35 mm×1 mm. The lab-on-a-chip device 700, shown in FIG. 7A, includes an air pump inlet 702, a hydrophobic passive valve 704, a sample loading well 710, a sample loading channel 706, a hydrophobic passive valve 720, a detection antibody drying or lyophilization chamber 730, substrate drying or lyophilization chambers 740, 742, a delay channel 750, spiral reaction chambers 760, 762, 764, and a waste chamber 770.

In embodiments, the sample flow in the lab-on-a-chip device 700 is controlled by the air pressure from a pump connected to the air pump inlet 702. In the lab-on-a-chip device 700, the sample reconstituted reagents in the detection antibody drying or lyophilization chamber 730, and in the substrate drying or lyophilization chambers 740, 742. The sample carries the reconstituted reagents into the spiral reaction chambers 760, 762, 764. Each of the spiral reaction chambers 760, 762, 764 has a width of 350 µm, a depth of 250 µm, a length of 45.7 mm and a volume of 4 µL. Each spiral reaction chamber has an outer diameter of 6.5 µm, comparable to the diameter of each well of a conventional 96-well plate. Also, the distance between each of the spiral reaction chambers is 9 mm, similar to the distance between each of the wells of a 96-well plate. The similarity in the dimensions between the 96-well plate and the spiral reaction chambers 760, 762, 764 of the lab-on-a-chip device 700 helps in characterization of the lab-on-a-chip device 700.

Each reaction chamber has a volume of 4 μL and a surface-to-volume ratio of 137.5 cm−1 whereas the surface-to-volume ratio of each of the wells of a 96-well plate is 9.6 cm−1. Thus, the surface-to-volume ratio of each of the spiral reaction chambers 760, 762, 764 is almost 15 times higher than that of each well of a 96-well plate. The high surface-to-volume ratio results in a higher amount of capture antibody immobilization, which results in high optical signal output with small (μL) analyte volumes having very low (pg/mL) antigen concentrations.

To control the flow of sample on the lab-on-a-chip device 700, the hydrophobic passive valves 704, 720 are added as shown in FIG. 7A. The hydrophobic passive valves 704, 720 control the direction of flow, the reagent reconstitution and incubation. The detection antibody drying or lyophilization chamber 730, and the substrate drying or lyophilization chambers 740, 742 are designed so as to facilitate pre-loading and lyophilization of the reagents. Circular posts in the detection antibody drying or lyophilization chamber 730, and the substrate drying or lyophilization chambers 740, 742 facilitates uniform drying by creating numerous small menisci. As shown in FIG. 7A, the hydrophobic passive valves 704, 720 and the delay channel 750 prevent the unintentional and uncontrolled flow of the sample in the absence of air pressure from an external pump. The hydrophobic passive valve 720 placed before the substrate drying and lyophilization chamber 740 ensures that the sample first fills up the detection antibody drying or lyophilization chamber 730, and then fills up the substrate drying or lyophilization chambers 740 and 742.

The passive valves at the end of each of the detection antibody drying or lyophilization chamber 730 and the substrate drying or lyophilization chambers 740, 742 coupled with the air flow control by the pump allow proper reconstitution and incubation of the reagents in the chambers. The delay channel 750 after the substrate drying or lyophilization chambers 740, 742 ensures that the antigen-detection antibody complex enters the reaction chambers 760, 762, 764 and binds with the immobilized capture antibody before the reconstituted substrate enters the reaction chambers 760, 762, 764. The lab-on-a-chip device 700 is designed to minimize user intervention and simplify sample introduction. A user only needs to drop a sample into the sample loading well 710. The sample containing the antigen is loaded into the sample loading well 710 by peeling a detachable and attachable tape on the sample loading well 710, dropping the sample, and sealing the tape. This sample loading process reduces the complexity of the lab-on-a-chip device 700 by removing the sample pipetting step and thus renders it more user-friendly. The detailed dimensions of the spiral reaction chamber and all the reagent chambers are given in Table 2.

TABLE 2

| CHAMBERS | WIDTH | LENGTH | HEIGHT | VOLUME |
| --- | --- | --- | --- | --- |
| Detection antibody Chamber | 3 mm | 15.9 mm | 350 μm | 16.5 μL |
| Chemiluminescent Chamber (1 & 2) | 3 mm | 8.5 mm | 350 μm | 8.9 μL |
| Each of the Spiral Reaction Chamber | 350 μm | 45.7 mm | 250 μm | 4 μL |
| Sample Loading Chamber | 4 mm | 27 mm | 350 μm | 37.8 μL |

FIG. 7B depicts a flowing sequence of a sample in the chip, according to one or more embodiments shown and described herein. In step (i), provided is a microfluidic chip where the enzyme labelled detection antibody and the chemiluminescent substrate are dried or lyophilized in isolated chambers (e.g., the detection antibody drying or lyophilization chamber 730, the substrate drying or lyophilization chambers 740, 742 in FIG. 7A) prior to sample addition. In embodiments, first, 15 μL of the HRP conjugated detection antibody is loaded onto the detection antibody chamber. Then, 7.5 μL of peroxide and 7.5 μL of enhancer of substrate (e.g., the SuperSignal Femto ELISA chemiluminescent substrate (37075, Thermo Fisher Scientific Inc., USA)) is separately loaded onto their respective substrate chambers (e.g., the substrate drying or lyophilization chambers 740, 742 in FIG. 7A). The reagent loaded on the lab-on-a-chip device 700 is pre-frozen in liquid nitrogen and subsequently lyophilized. The lab-on-a-chip device 700 is lyophilized for 24 hours in a freeze dryer (e.g., the Labconco™ Freeze Dryer (Labconco, USA)) at −54° C. and 0.010 mbar pressure. The lab-on-a-chip device 700 with the lyophilized reagent is then solvent bonded. After bonding, a 12 μL, solution containing the optimized concentration of capture antibody is coated onto the spiral reaction chambers by surface immobilization. The lab-on-a-chip device 700 is then blocked using buffer solution (e.g., DY995, R&D Systems, USA).

In step (ii), the sample reconstitutes both the detection antibody and the substrate. Specifically, the sample reconstitutes the dried or lyophilized detection antibody in the detection antibody drying or lyophilization chamber 730 and the dried or lyophilized substrates in the substrate drying or lyophilization chamber 740, 742.

In step (iii), the sample reconstituted antigen-antibody complex reaches the reaction chambers (e.g., the reaction chambers 760, 762, 764 in FIG. 7A) earlier than the reconstituted substrate. In step (iv), the reconstituted substrate finally reaches the reaction chambers causing the enzyme-substrate reaction generating chemiluminescence.

Figure 8A:
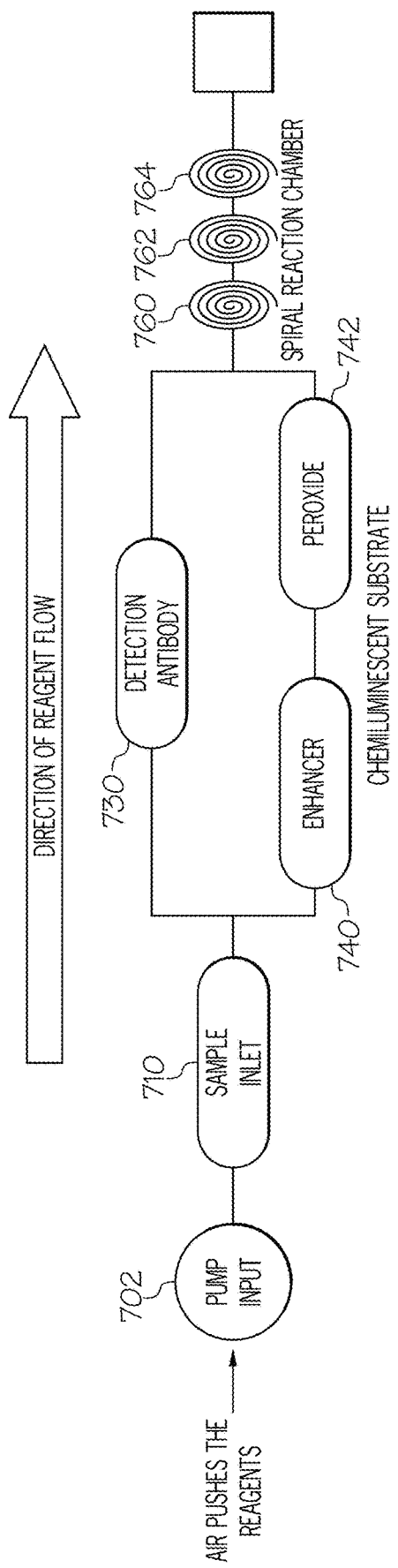
FIG. 8A depicts the schematic of the air driven on-chip sample delivery process, according to one or more embodiments shown and described herein.
Figure 8B:
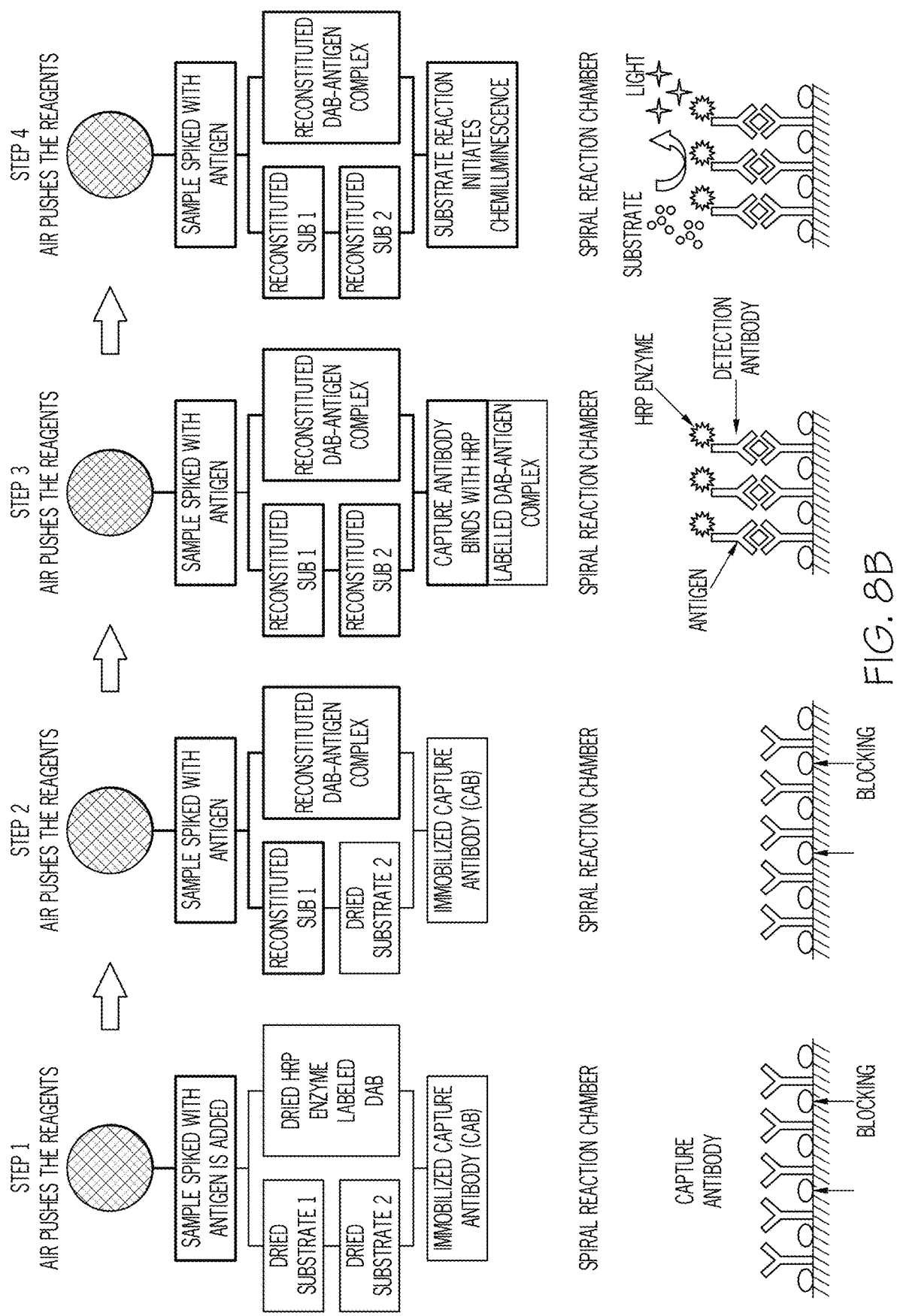
FIG. 8B depicts the schematic of the air driven on-chip sample delivery process, according to one or more embodiments shown and described herein.

The chemiluminescent sandwich ELISA protocol according to the present disclosure is illustrated in FIGS. 8A and 8B. The schematic of the air driven on-chip sample delivery process used is illustrated in FIG. 8A. The sample with TNF-α antigen was added and the external pump is connected to the air pump inlet 702 of the lab-on-a-chip device 700. Step 1 of FIG. 8B depicts that the sample is added in the sample loading well 710. Capture antibodies are attached to the inner wall of the microfluidic channels of the spiral reaction chambers 760, 762, 764. Buffer solution blocks gaps between capture antibodies.

In step 2 of FIG. 8B, an air pump provides air that pushes the sample to enter the detection antibody drying or lyophilization chamber 730 and reconstitute the HRP-conjugated detection antibodies dried or lyophilized in the detection antibody drying or lyophilization chamber 730. The sample entering the substrate drying or lyophilization chambers 740, 742 reconstitutes the dried or lyophilized enhancer and peroxide sequentially and moves towards the spiral reaction chamber 760, 762, 764.

In step 3 of FIG. 8B, air continues to push the reagents in the lab-on-a-chip device 700, and the reconstituted HRP-conjugated detection antibodies flow into the spiral reaction chambers 760, 762, 764 before the reconstituted substrates reach the spiral reaction chambers 760, 762, 764 due to the delay channel 750 shown in FIG. 7A. The capture antibodies attached to the inner wall of the microfluidic channels of the spiral reaction chambers 760, 762, 764 bind with the reconstituted HRP-conjugated detection antibodies as shown in step 3 of FIG. 8B.

In step 4 of FIG. 8B, air continues to push the reagents in the lab-on-a-chip device 700, and the reconstituted substrates flow into the spiral reaction chambers 760, 762, 764. The reconstituted substrates (i.e., chemiluminescent substrates) react with the HRP enzyme of the HRP-conjugated detection antibodies to yield an optical signal as shown in step 4 of FIG. 8B.

Figure 9A:
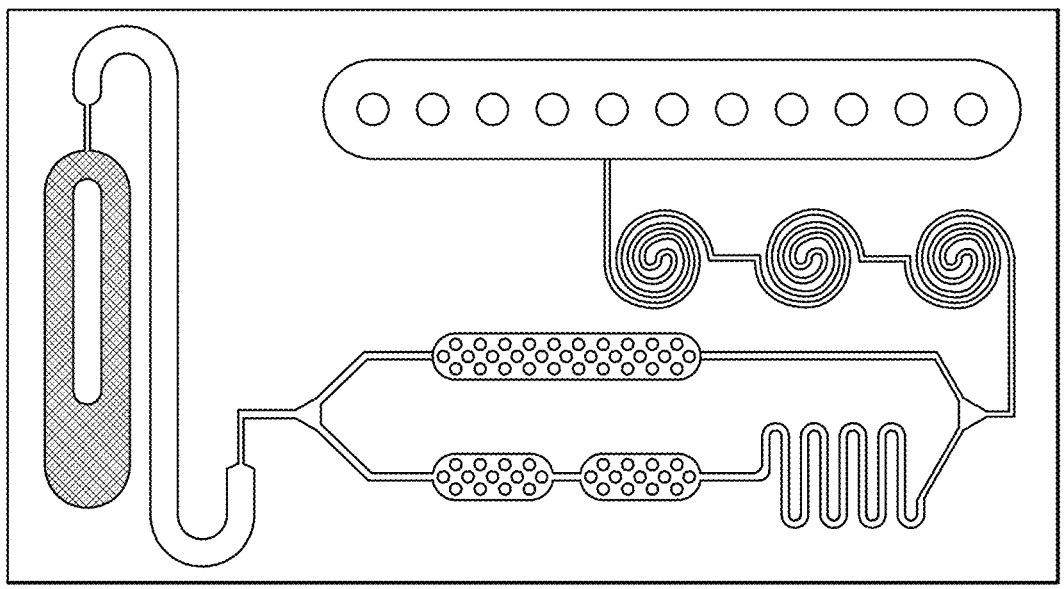
FIG. 9A depicts an exemplary on-chip sample and reagent flow sequence for chemiluminescent, according to one or more embodiments shown and described herein.

FIGS. 9A through 9D depict an exemplary on-chip sample and reagent flow sequence for chemiluminescent, according to one or more embodiments shown and described herein. As shown in FIG. 9A, the hydrophobic passive valve 704 placed after the sample loading well 710 (FIG. 7A) and the sample loading channel 706 prevent the unintentional and uncontrolled flow of the sample into the reagent reservoirs (e.g., the detection antibody drying or lyophilization chamber 730, the substrate drying or lyophilization chambers 740, 742) in the absence of air pressure from an external pump. After the sample containing antigen is introduced, an external pump is connected to the air pump inlet 720 (FIG. 7A) of the lab-on-a-chip device 700.

Figure 9B:
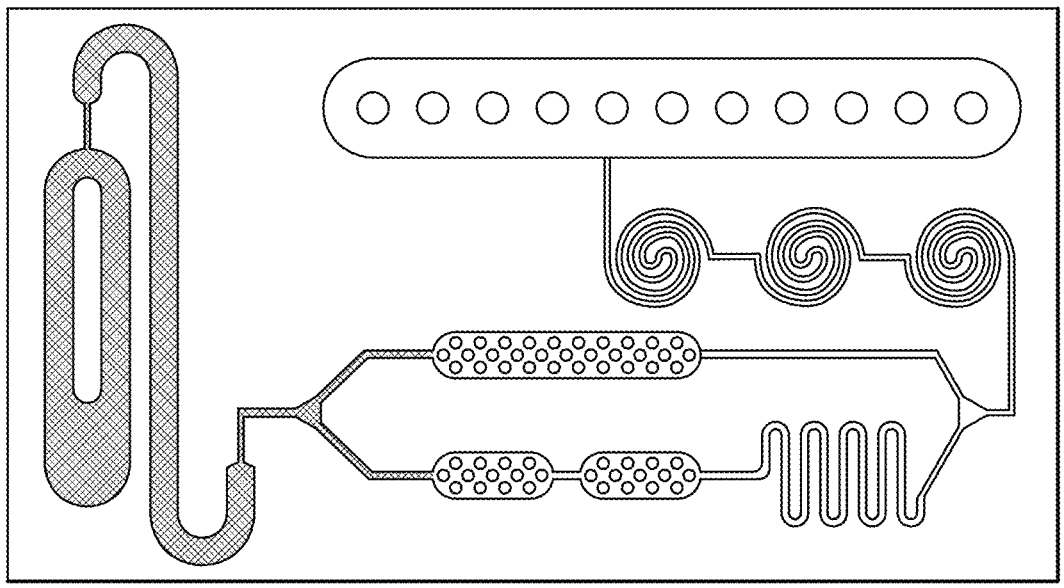
FIG. 9B depicts an exemplary on-chip sample and reagent flow sequence for chemiluminescent, according to one or more embodiments shown and described herein.

As shown in FIG. 7A, the hydrophobic passive valve 720 is placed at the entrance of the substrate drying or lyophilization chamber 740. Due to the presence of the hydrophobic passive valve 720 placed before the substrate drying or lyophilization chamber 740, the pressure drop across the detection antibody drying and lyophilization chamber 730 exceeds the pressure drop across the substrate drying or lyophilization chambers 740, 742. Therefore, the sample first fills up the detection antibody drying or lyophilization chamber 730 as shown in FIG. 9B.

Figure 9C:
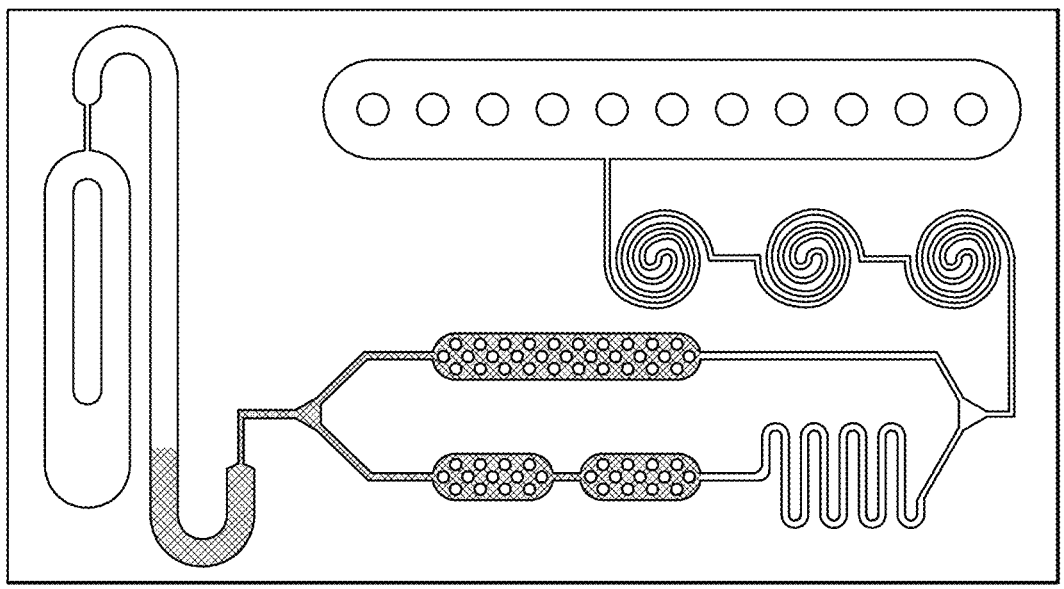
FIG. 9C depicts an exemplary on-chip sample and reagent flow sequence for chemiluminescent, according to one or more embodiments shown and described herein.

After the detection antibody drying or lyophilization chamber 730 is filled up, the pressure drops across the hydrophobic passive valve 752 at the exit of the detection antibody drying or lyophilization chamber 730 becomes less than the pressure drops across the substrate drying or lyophilization chambers 740, 742. The sample then fills up the substrate drying or lyophilization chambers 740, 742 as shown in FIG. 9C. At this point the external pump is turned off to allow reconstitution and incubation of the reagents in the detection antibody drying or lyophilization chamber 730, and the substrate drying or lyophilization chambers 740, 742. During this incubation period, the antigens in the sample bind with the reconstituted HRP-conjugated detection antibodies.

Figure 9D:
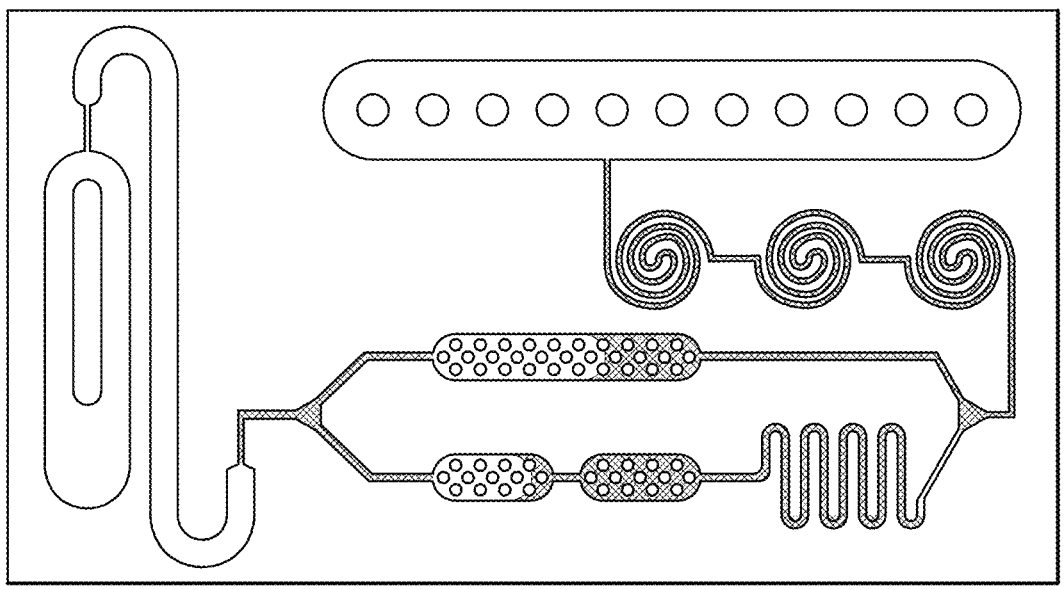
FIG. 9D depicts an exemplary on-chip sample and reagent flow sequence for chemiluminescent, according to one or more embodiments shown and described herein.

After an incubation period of 10 minutes, the external pump is turned on. The reconstituted and incubated sample then starts flowing towards the spiral reaction chamber 760, 762, 764. The delay channel 750 after the substrate drying or lyophilization chambers 740, 742 ensures that the antigen-detection antibody complex enters the spiral reaction chambers 760, 762, 764 and binds with the immobilized capture antibody before the reconstituted substrate enters the spiral reaction chamber 760, 762, 764 as shown in FIG. 9D. The reconstituted chemiluminescent substrate then reacts with the HRP enzyme of the reconstituted detection antibody to yield an amplified optical signal.

Figures 10A, 10B, 10C:
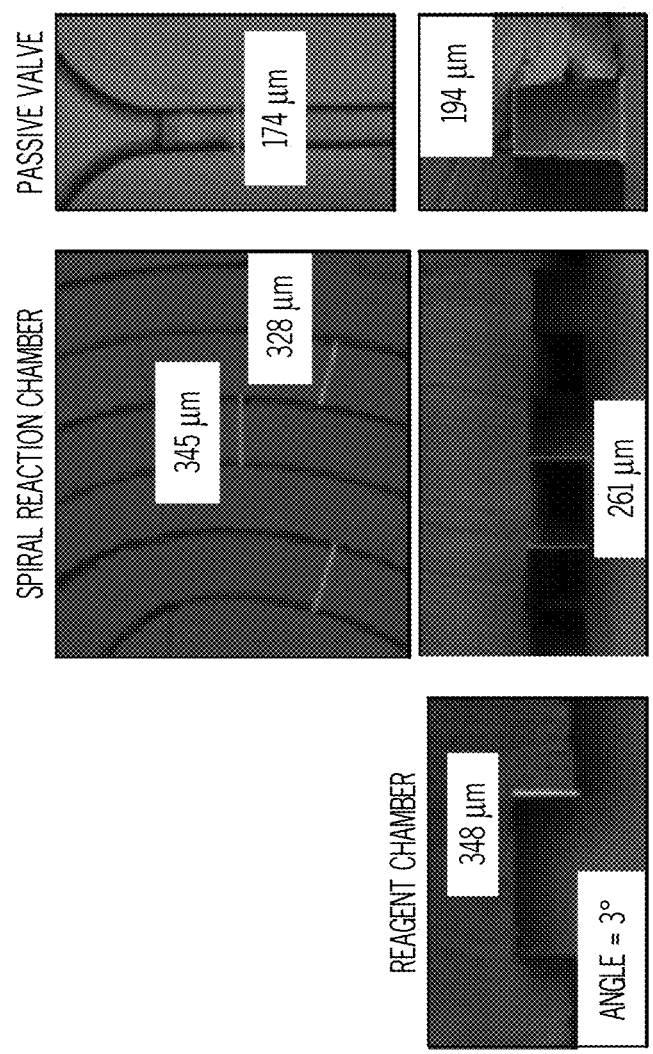
FIG. 10A depicts the structural analysis picture of a reagent chamber of aluminum micromold.
FIG. 10B depicts the structural analysis picture of a spiral reaction chamber of aluminum micromold.
FIG. 10C depicts the structural analysis picture of a hydrophobic passive valve of aluminum micromold.

FIGS. 10A through 10C depict the structural analysis pictures from an inverted microscope (e.g., Olympus ix-71). The fabricated Aluminum master mold and the COC lab-on-a-chip device are characterized to evaluate the reproducibility of the CNC milling process and the injection molding replication process. The measured height of the reagent chambers of 348 μm is 99.43% of the designed height. The width of the channels of the reaction chamber and the channel to channel distance is measured to be 345 μm and 328 μm, respectively. The measured dimensions are 98.6% and 93.7% of the intended dimensions. The height of the reaction chamber of 261 μm is 104.4% of the intended height of the reaction chamber. The width and the height of the passive valves are measured to be 174 μm and 193 μm, which are 102.4% and 96.5% of the intended design, respectively. A 2° draft angle is introduced in the design, whereas the measured draft angle is 3°.

FIGS. 11A through 11C depict the structural analysis pictures of a replicated lab-on-a-chip device from an inverted microscope. The height of the replicated reagent chamber is measured to be 361 μm which is 103.1% of the dimensions of the designed reagent chambers, as shown in FIG. 11A. The width of the channels of the spiral reaction chambers and the channel to channel distance are measured to be 364 μm and 332 μm, respectively. The measured dimensions are 104% and 94.8% of the intended dimensions, as shown in FIG. 11B. The height of the spiral reaction chamber of 248 μm is 99.2% of the intended height of the spiral reaction chamber. The width of the hydrophobic passive valve is 164 μm, as shown in FIG. 11C, which is 96.5% of the designed width. The height of the passive valves is measured to be 206 μm, which is 102.4% of the height of designed chambers. The measured draft angle is 5° as shown in FIG. 11A.

In embodiments, the concentration and incubation periods of the capture antibody, detection antibody, HRP and chemiluminescent substrate in the present lab-on-a-chip device (e.g., the lab-on-a-chip device 200 and the lab-on-a-chip device 700) are optimized to obtain the highest on-chip output signal. The optimized concentration and incubation time is shown in the table 3 below.

TABLE 3

|  | Concentration | Incubation/Reconstitution Time |
|---|---|---|
| Capture Antibody | 8 μg/ml | 20 minutes |
| Detection Antibody | 0.2 μg/ml | 10 minutes |
| HRP | 120 fold dilution | NA |
| Chemiluminescent Substrate | NA | 10 minutes |

The TNF-α sandwich ELISA is performed using the present lab-on-a-chip device. The lyophilized reagent-based sandwich ELISA protocol described above is used. The optimized concentrations and incubation periods described above are used for the assay. The TNF-α antigen concentration range used is from 2 to 4,000 pg/mL.

Figure 12B:
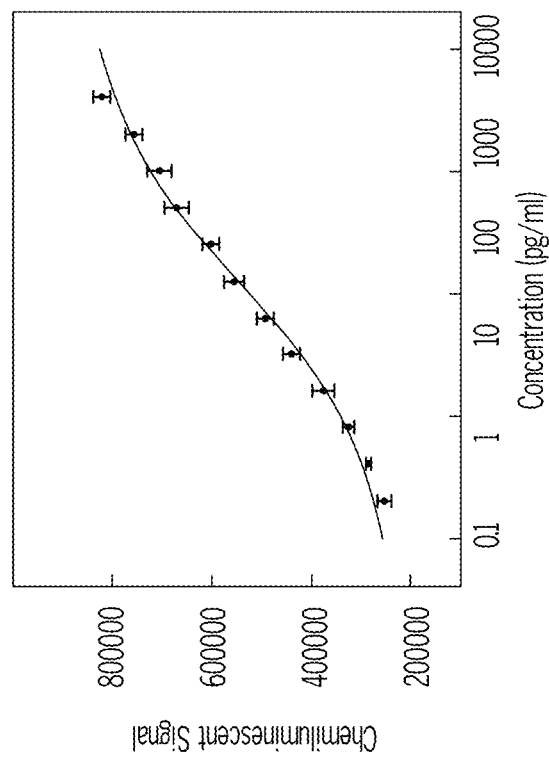
FIG. 12B depicts the chemiluminescent signal obtained from the assay performed using the present lab-on-a-chip device.
Figure 12A:
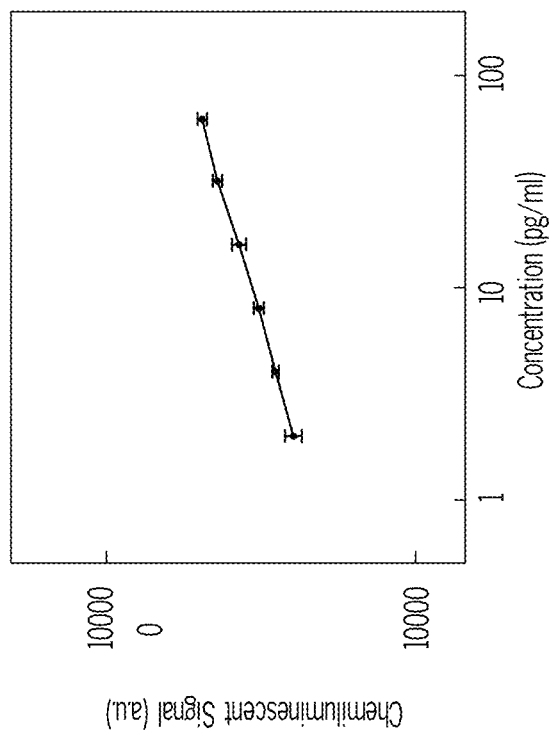
FIG. 12A depicts the chemiluminescent signal obtained from the assay performed using the present lab-on-a-chip device.

FIGS. 12A and 12B depicts the chemiluminescent signal obtained from the assay performed using the present lab-on-a-chip device. An LOD of 3.15 pg/mL is obtained from the standard curve shown in FIG. 12B. The average assay CV is calculated to be around 5-8%. Also, a linear trend is observed across the lower TNF-α concentration range of 2-62 pg/mL as shown in FIG. 12A.

The number of capture antibodies immobilized onto the surface of the spiral reaction chamber of the present lab-on-a-chip device is greater than that of each of the well of the 96-well plate. This is because the spiral reaction chamber has 15 times higher surface to volume ratio. Due to that, a large number of antigen binding sites are available. Therefore, even very low concentration of TNF-α antigen present in the sample can specifically bind to the capture antibodies. This increases the detectable concentration range for the assay by 10 to 12 folds. The LOD obtained from the lyophilized reagent-based LOC assay is almost 14 times less than the LOD obtained from the conventional 96-well plate assay. The concentration of TNF-α in the blood/serum of patients with pulmonary diseases caused due to airborne respirable nano or micro particle exposure changes from several pico-gram to several nano-gram. Due to the wide detectable concentration range obtained, the present lab-on-a-chip device can specifically identify the presence of TNF-α during any stages of airborne respirable nano or micro particle exposure. Also, the linear trend in the lower concentration range of 1 to 62 pg/mL and the lower LOD of around 1 pg/mL prove that the present lab-on-a-chip device can successfully detects the presence of several picogram of TNF-α. The performance of the present lab-on-a-chip device is considered suitable for early detection of lung inflammation due to airborne respirable nano or micro particle exposure because TNF-α concentration above 1-5 pg/mL in plasma indicates the on-set of a toxic pulmonary response.

Figure 13A:
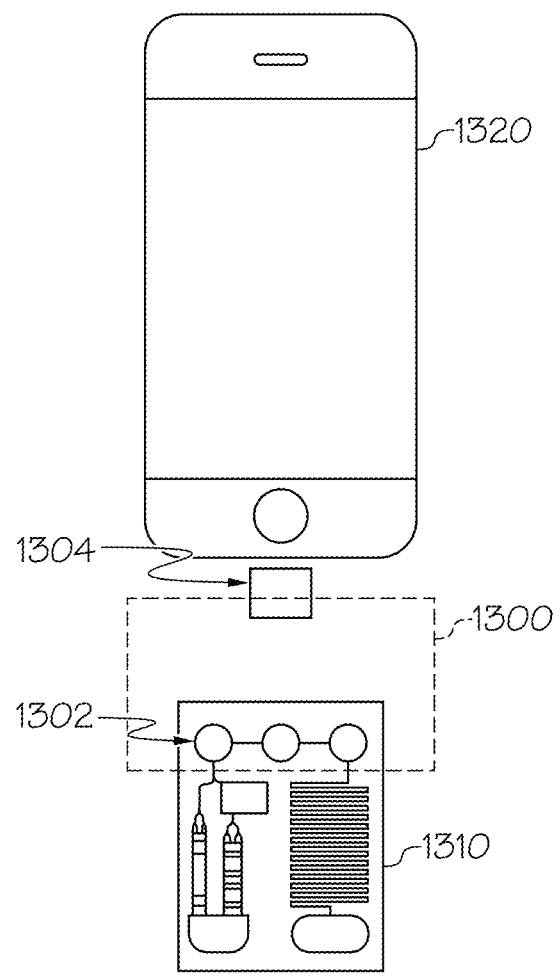
FIG. 13A depicts schematic of the present lab-on-a-chip device interfacing with an analyzer circuit powered by a smartphone, according to one or more embodiments shown and described herein.
Figure 13B:
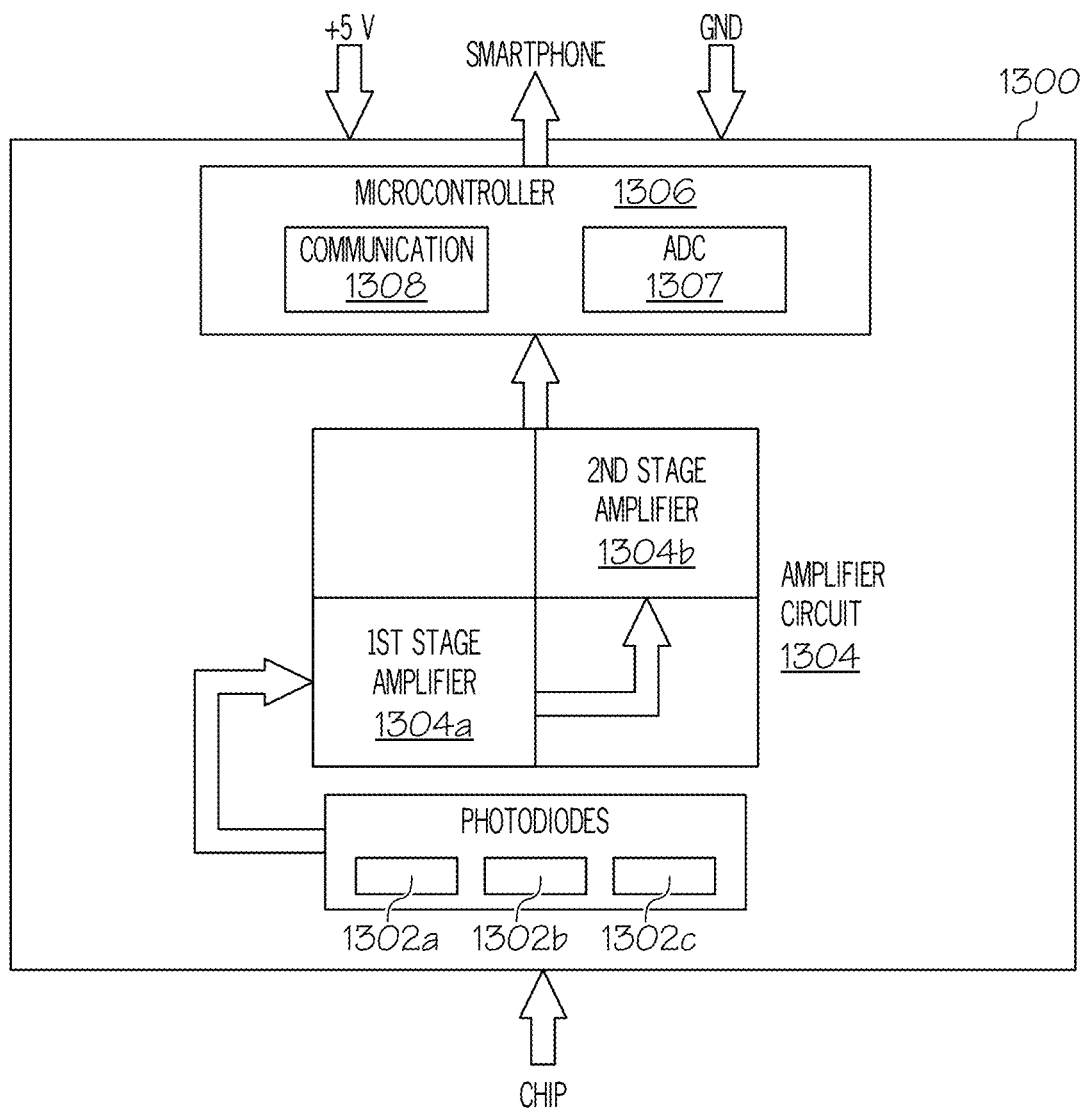
FIG. 13B depicts an analyzer system with 3D printed housing, according to one or more embodiments shown and described herein.

FIG. 13A depicts schematic of the present lab-on-a-chip device (e.g., the lab-on-a-chip device 200 or 700) interfacing with an analyzer circuit powered by a smartphone, according to one or more embodiments shown and described herein. FIG. 13B depicts an analyzer system with 3D printed housing, according to one or more embodiments shown and described herein.

As shown in FIGS. 13A and 13B, a sensing system includes a lab-on-a-chip device 1310, an analyzer chip 1301, and a mobile device 1320. The optical signal from the lab-on-a-chip device 1310 is detected by photodiodes 1302 of the analyzer chip 1301. The lab-on-a-chip device 1310 may be the lab-on-a-chip device 200 shown in FIG. 2 or the lab-on-a-chip device shown in FIG. 7A. The analyzer chip 1310 communicates with a mobile device 1320 through the USB interface 1305.

Specific examples of the mobile device 1320 include, but are not limited to, smart phones, tablet devices, e-readers, laptop computers, or the like. The mobile device 1320 may receive assay data from the analyzer chip 1301 and display the assay data on the screen of the mobile device 1320. In embodiments, the mobile device 1320 may power the analyzer chip 1301. The lack of an external power source enhances the portability of the system. In embodiments, blood samples from malaria infected population may be used and the corresponding assay data validates the reliability of the developed point of care (POC) system.

The working principle of the sensing system 1300 is to detect the chemiluminescent light emitted from the spiral reaction chambers of the lab-on-a-chip device 1310 in the form of photocurrent, amplify the photocurrent, convert the photocurrent into digital format for communication with the mobile device 1320, and display the information extracted from the raw data on the mobile device 1320. A portable mechanical assembly may house the analyzer chip 1301 and the lab-on-a-chip device 1310. The analyzer chip 1301 may be powered from the USB port of the mobile device 1320 using the On-The-Go (OTG) protocol.

The analyzer chip 1301 may detect and amplify optical signals from the lab-on-a-chip device 1310. The light emitted by the three spiral reaction chambers of the lab-on-a-chip device 1310 may be captured and converted into current by photodiodes 1302a, 1302b, 1302c placed very close to the spiral reaction chambers. The low magnitude current owing to the low intensity of the emitted chemiluminescent light requires the need for an amplification stage. A amplifier circuit 1304 may amplifies the current received from the photodiodes 1302a, 1302b, 1302c. Specifically, trans-impedance amplifiers, characterized with high gain-bandwidth and low noise performance may be used to provide two-stage amplification. A first stage amplifier 1304a and a second stage amplifier 1304b convert the received current into a higher magnitude voltage, respectively. The voltage may be passed through a low-pass filter to remove any high frequency noise components.

The analyzer chip 1301 includes a microcontroller 1306 having an analog to digital converter 1307 and a communication interface 1308. The filtered analog voltage may be fed to the analog to digital converter 1307 of the microcontroller 1306 to obtain digital data which is then transmitted from the microcontroller 1306 to the mobile device 1320 for processing, via the USB interface 1305. The USB interface 1305 may work as a power supplier. The USB interface 1305 may provide control signals from the mobile device 1320 to the microcontroller 1306 and transfer data from the microcontroller 1306 to the mobile device 1320 in real time.

Figure 14:
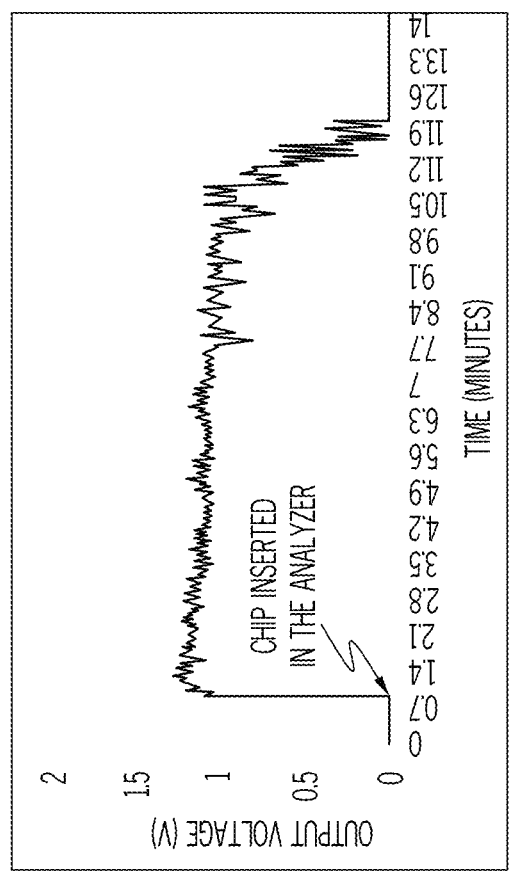
FIG. 14 depicts an output voltage signal from an analyzer chip, according to one or more embodiments shown and described herein.

The mobile device 1320 may act as a host to the portable analyzer, employing the USB on-the-go feature. In embodiments, the mobile device 1320 is a smart phone, and a custom application may be used to acquire the raw data, process the raw data to remove any random and unwanted data, plot a voltage versus time graph, and obtain the voltage value from the graph which corresponds to intensity of the light from the spiral reaction chambers. The voltage value may be used against a reference concentration versus voltage graph (obtained through repeated experiments with a range of known antigen concentrations) to obtain an unknown biomarker concentration value and display related information to a user. The output voltage signal from the analyzer chip 1301 is shown in FIG. 14.

The analyzer chip 1301 may work on a +5V power supply provided by the mobile device 1320 via the USB interface 1305, removing the need for a battery. The USB based communication provides a faster and more secure means of data transfer than other communication protocols. The sensing system 1300 involves less power consumption from the smartphone battery than wireless communication.

It should be understood that embodiments described herein provide a portable, easy-to-use, miniaturized polymer functional lab-on-a-chip device. The lab-on-a-chip device utilizes on-chip lyophilized reagents to perform sandwiched ELISA. The lab-on-a-chip device may be utilized for testing Tumor necrosis factor-α (TNF-α), a biomarker related to pulmonary effects caused by exposure of toxic airborne respirable nano or micro particles. Micromachining of Aluminum master mold and injection molding based low-cost, mass producible fabrication technique are optimized for high precision replication. The lyophilized reagent-based lab-on-a-chip device according to the present disclosure is designed in such a way that the sample flow may be controlled by a pump. The lyophilized reagent based on-chip ELISA are characterized using Tumor necrosis factor-α (TNF-α), one of the biomarkers for lung inflammation caused due to airborne respirable nano or micro particle exposure. The results obtained from the present lab-on-a-chip device with TNF-α spiked artificial serum showed high sensitivity in the complete concentration range of 1 pg/mL to 4 ng/mL. The detectable linear response of the chemiluminescent output signal observed for TNF-α concentration range below 62 pg/mL makes the present lab-on-a-chip device suitable for early detection of the target biomarker for pulmonary diseases.

It is to be further understood that where descriptions of various embodiments use the term "comprising," and/or "including" those skilled in the art would understand that in some specific instances, an embodiment can be alternatively described using language "consisting essentially of" or "consisting of."

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

What is claimed is:

1. A sensing device comprising:
   a sample loading chamber configured to receive a sample;
   a detection antibody drying or lyophilization chamber configured to receive a first portion of the sample;
   one or more substrate drying or lyophilization chambers configured to receive a second portion of the sample;
   one or more reaction chambers connected to the detection antibody drying or lyophilization chamber and the one or more substrate drying or lyophilization chambers; and
   a delay channel between the one or more substrate drying or lyophilization chambers and the one or more reaction chambers,
   wherein the detection antibody drying or lyophilization chamber and one or more substrate drying or lyophilization chambers are placed in parallel between the sample loading chamber and the one or more reaction chambers.

2. The sensing device of claim 1, further comprising a hydrophobic passive valve between the sample loading chamber and the one or more substrate drying or lyophilization chambers,
   wherein the hydrophobic passive valve prevents the second portion of the sample from flowing into the one or more substrate drying or lyophilization chambers before the first portion of the sample fills the detection antibody drying or lyophilization chamber.

3. The sensing device of claim 1, wherein the one or more substrate drying or lyophilization chambers comprise a chamber including dried or lyophilized enhancer and a chamber including dried or lyophilized peroxide.

4. The sensing device of claim 1, wherein the sample loading chamber comprises an air pump inlet.

5. The sensing device of claim 1, wherein the detection antibody drying or lyophilization chamber comprises a plurality of circular posts.

6. The sensing device of claim 1, wherein the one or more substrate drying or lyophilization chambers comprise a plurality of circular posts.

7. The sensing device of claim 1, wherein each of the one or more reaction chambers comprises a spiral microfluidic channel.

8. The sensing device of claim 7, wherein the spiral microfluidic channel comprises immobilized capture antibody.

9. The sensing device of claim 7, wherein an outer diameter of each of the one or more reaction chambers is about 6.5 millimeters.

10. The sensing device of claim 1, wherein the sample loading chamber comprises:
    a sample loading port;
    a sample loading channel; and
    a hydrophobic passive valve connected between the sample loading port and the sample loading channel.

11. The sensing device of claim 1, wherein the detection antibody drying or lyophilization chamber comprises dried or lyophilized detection antibodies, and the one or more substrate drying or lyophilization chambers comprise dried or lyophilized substrates or substrate components.

12. The sensing device of claim 1, further comprising:
    a first set of capillary channels between the sample loading chamber and the one or more substrate drying or lyophilization chambers; and
    a second set of capillary channels between the sample loading chamber and the detection antibody drying or lyophilization chamber.

13. The sensing device of claim 12, further comprising:
    a first multiplexing capillary channel between the one or more substrate drying or lyophilization chambers and the one or more reaction chambers; and
    a second multiplexing capillary channel between the detection antibody drying or lyophilization chamber and the one or more reaction chambers.

14. The sensing device of claim 13, wherein the one or more substrate drying or lyophilization chambers comprise a first substrate drying or lyophilization chamber and a second substrate drying or lyophilization chamber, and
    the sensing device comprises a third set of capillary channels between the first substrate drying or lyophilization chamber and the second substrate drying or lyophilization chamber.

15. The sensing device of claim 14, further comprising:
    a first descending passageway between the first set of capillary channels and the first substrate drying or lyophilization chamber;
    a first ascending passageway between the first substrate drying or lyophilization chamber and the third set of capillary channels;
    a second descending passageway between the third set of capillary channels and the second substrate drying or lyophilization chamber; and
    a second ascending passageway between the second substrate drying or lyophilization chamber and the first multiplexing capillary channel.

16. The sensing device of claim 14, further comprising:
    a descending passageway between the second set of capillary channels and the detection antibody drying or lyophilization chamber; and
    an ascending passageway between the detection antibody drying or lyophilization chamber and the second multiplexing capillary channel.

17. The sensing device of claim 12, further comprising:
    a capillary pump; and
    a delay channel connected between the one or more reaction chambers and the capillary pump.

18. A method of testing a sample on the sensing device according to claim 1, wherein the device of claim 1 further comprises an air pump, the method comprising:
    providing the sample in the sample loading chamber;
    turning on the air pump to provide air to the sample in the sample loading chamber such that the first portion of the sample flows into the detection antibody drying or lyophilization chamber and the second portion of the sample flows into the one or more substrate drying or lyophilization chamber and the second portion of the sample flows into the one or more substrate drying or lyophilization chambers after the first portion of the sample flows into the detection antibody drying or lyophilization chamber;
    turning off the air pump for a predetermined time; and
    turning on the air pump, after the predetermined time, to provide air to the sample such that the first portion of the sample flows into the one or more reaction chambers, and the second portion of the sample flows into the one or more reaction chambers after the first portion of the sample flows into the one or more reaction chambers.

19. The method of claim 18, wherein the sensing device further comprises a hydrophobic passive valve between the sample loading chamber and the one or more substrate drying or lyophilization chambers, wherein the hydrophobic passive valve prevents the second portion of the sample from flowing into the one or more substrate drying or lyophilization chambers before the first portion of the sample fills the detection antibody drying or lyophilization chamber.

20. The method of claim 18, wherein each of the one or more reaction chambers comprises a spiral microfluidic channel.

21. The method of claim 18, wherein the detection antibody drying or lyophilization chamber comprises dried or lyophilized detection antibodies, and the one or more substrate drying or lyophilization chambers comprise dried or lyophilized substrates or substrate components.

22. A sensing system comprising:
a sensing device comprising:
   a sample loading chamber configured to receive a sample;
   a detection antibody drying or lyophilization chamber comprising dried or lyophilized detection antibodies, the detection antibody drying or lyophilization chamber being configured to receive a first portion of the sample;
   one or more substrate drying or lyophilization chambers comprising dried or lyophilized substrates, the one or more substrate drying or lyophilization chambers being configured to receive a second portion of the sample;
   one or more reaction chambers connected to the detection antibody drying or lyophilization chamber and the one or more substrate drying or lyophilization chambers; and
   a delay channel between the one or more substrate drying or lyophilization chambers and the one or more reaction chambers,
   wherein the detection antibody drying or lyophilization chamber and one or more substrate drying or lyophilization chambers are placed in parallel between the sample loading chamber and the one or more reaction chambers; and
an analyzer configured to detect optical signals from the one or more reaction chambers.

23. The sensing system of claim 22, wherein the analyzer comprises one or more photodiodes configured to detect optical signals from the one or more reaction chambers, respectively.

24. The sensing system of claim 22, wherein the analyzer comprises a USB interface configured to receive power from an external device.

* * * * *